(12) United States Patent
Allison

(10) Patent No.: US 7,693,257 B2
(45) Date of Patent: Apr. 6, 2010

(54) TREATMENT DELIVERY OPTIMIZATION

(75) Inventor: John W. Allison, Los Altos, CA (US)

(73) Assignee: Accuray Incorporated, Sunnyvale, CA (US)

( * ) Notice: Subject to any disclaimer, the term of this patent is extended or adjusted under 35 U.S.C. 154(b) by 179 days.

(21) Appl. No.: 11/480,003

(22) Filed: Jun. 29, 2006

(65) Prior Publication Data

US 2008/0002811 A1  Jan. 3, 2008

(51) Int. Cl.
*A61N 5/10* (2006.01)

(52) U.S. Cl. .................................. 378/65; 378/108

(58) Field of Classification Search ............... 378/207, 378/64–65, 108–112, 97
See application file for complete search history.

(56) References Cited

U.S. PATENT DOCUMENTS

| | | | |
|---|---|---|---|
| 4,233,667 A | 11/1980 | Devine et al. | |
| 4,414,547 A | 11/1983 | Knapp et al. | |
| 4,489,857 A | 12/1984 | Batlas | |
| 4,720,778 A | 1/1988 | Hall et al. | |
| 4,918,440 A | 4/1990 | Furtek et al. | |
| 5,212,716 A | 5/1993 | Ferraiolo et al. | |
| 5,311,079 A | 5/1994 | Ditlow et al. | |
| 5,392,437 A | 2/1995 | Matter et al. | |
| 5,652,529 A | 7/1997 | Gould et al. | |
| 5,737,516 A | 4/1998 | Circello et al. | |
| 5,754,622 A * | 5/1998 | Hughes | 378/65 |
| 5,841,973 A | 11/1998 | Cooke et al. | |
| 5,892,962 A | 4/1999 | Cloutier | |
| 5,926,638 A | 7/1999 | Inoue | |
| 5,960,200 A | 9/1999 | Eager et al. | |
| 5,996,083 A | 11/1999 | Gupta et al. | |
| 6,003,143 A | 12/1999 | Kim et al. | |
| 6,038,284 A * | 3/2000 | Hernandez-Guerra et al. | 378/65 |
| 6,058,469 A | 5/2000 | Baxter | |
| 6,170,051 B1 | 1/2001 | Dowling | |
| 6,211,697 B1 | 4/2001 | Lien et al. | |
| 6,212,650 B1 | 4/2001 | Guccione | |
| 6,282,701 B1 | 8/2001 | Wygodny et al. | |
| 6,286,134 B1 | 9/2001 | Click, Jr. et al. | |
| 6,301,706 B1 | 10/2001 | Maslennikov et al. | |
| 6,398,383 B1 | 6/2002 | Huang | |
| 6,421,809 B1 | 7/2002 | Wuytack et al. | |
| 6,434,695 B1 | 8/2002 | Esfahani et al. | |
| 6,434,699 B1 | 8/2002 | Jones et al. | |
| 6,435,054 B1 | 8/2002 | Duckeck et al. | |
| 6,437,441 B1 | 8/2002 | Yamamoto | |

(Continued)

FOREIGN PATENT DOCUMENTS

DE  38 55 673  11/1996

(Continued)

OTHER PUBLICATIONS

PCT International Search Report for PCT/US07/13035, Int'l. filing date May 31, 2007, Mailing date Apr. 3, 2008 (3 pgs.).

(Continued)

*Primary Examiner*—Hoon Song
(74) *Attorney, Agent, or Firm*—Blakely, Sokoloff, Taylor & Zafman LLP

(57) ABSTRACT

A method and apparatus to optimize delivery of radiation treatment.

49 Claims, 13 Drawing Sheets

U.S. PATENT DOCUMENTS

| | | |
|---|---|---|
| 6,490,695 B1 | 12/2002 | Zagorski et al. |
| 6,504,398 B1 | 1/2003 | Lien et al. |
| 6,542,844 B1 | 4/2003 | Hanna |
| 6,757,847 B1 | 6/2004 | Farkash et al. |
| 6,785,826 B1 | 8/2004 | Durham et al. |
| 6,961,924 B2 | 11/2005 | Bates et al. |
| 2001/0010074 A1 | 7/2001 | Nishihara et al. |
| 2002/0045952 A1 | 4/2002 | Blemel |
| 2002/0083308 A1 | 6/2002 | Pereira et al. |
| 2002/0138716 A1 | 9/2002 | Paul et al. |
| 2002/0150207 A1* | 10/2002 | Kapatoes et al. ............... 378/65 |
| 2003/0014743 A1 | 1/2003 | Cooke et al. |
| 2003/0192032 A1 | 10/2003 | Andrade et al. |
| 2004/0199688 A1 | 10/2004 | Vorbach et al. |
| 2006/0239415 A1* | 10/2006 | Liu et al. ..................... 378/207 |
| 2007/0165779 A1* | 7/2007 | Chen et al. ..................... 378/65 |

FOREIGN PATENT DOCUMENTS

| | | |
|---|---|---|
| EP | 0 398 552 | 11/1990 |
| EP | 0 696 001 | 12/2001 |
| FR | 2 752 466 | 2/1998 |
| JP | 58-58672 | 4/1983 |
| JP | 2-130023 | 5/1990 |
| JP | 2-226423 | 9/1990 |
| JP | 5-276007 | 10/1993 |
| JP | 7-154242 | 6/1995 |
| JP | 8-44581 | 2/1996 |
| JP | 8-250685 | 9/1996 |
| JP | 9-27745 | 1/1997 |
| JP | 11-307725 | 11/1999 |
| JP | 2000-181566 | 6/2000 |
| WO | WO92/01987 | 2/1992 |
| WO | WO99/12111 | 3/1999 |
| WO | WO01/55917 | 8/2001 |
| WO | WO02/21010 | 3/2002 |
| WO | WO02/071196 | 9/2002 |
| WO | WO03/025781 | 3/2003 |

OTHER PUBLICATIONS

PCT Written Opinion of the International Searching Authority for PCT/US07/13035, Int'l. filing date May 31, 2007, Mailing date Apr. 3, 2008 (8pgs.).

International Preliminary Report on Patentability (Chapter 1 of the Patent Cooperation Treaty), PCT/US2007/013035 filed May 31, 2007, mailed Jan. 15, 2009.

Coste-Manière, È., "Robotic whole body stereotacitc radiosurgery: clinical advantages of the CyberKnife® integrated system", The International Journal of Medical Robotics+Computer Assisted Sugery, 2005, www.roboticpublications.com, 14 pages.

Khan, Ph. D., Faiz M., "The Physics of Radiation Therapy", Third Edition, Lippincott Williams & Wilkins, 2003, title page, table of contents, and p. 159-198.

"Tissue Inhomogeneity Corrections for Megavoltage Photon Beams", AAPM Report No. 85, Medical Physics Publishing, Aug. 2004, ISBN: 1-888340-47-9.

Abnous, A., et al., "The Pleiades Architecture," Chapter 1 of the *The Application of Programmable DSPs in Mobile Communications*, A. Gatherer and A. Auslander, Ed., Wiley, 2002, pp. 1-33.

Athanas, "A Functional Reconfigurable Architecture and Compiler for Adoptive Computing," IEEE, pp. 49-55.

Beck et al., "From control flow to data flow," TR 89-1050, Oct. 1989, Dept. of Computer Science, Cornell University, Ithaca, NY, pp. 1 - 25.

Callahan, et al., "The Garp Architecture and C Compiler," Computer, Apr. 2000, pp. 62-69.

Chen et al., "A reconfigurable multiprocessor IC for rapid prototyping of algorithmic-specific high-speed DSP data paths," IEEE Journal of Solid-State Circuits, vol. 27, No. 12, Dec. 1992, pp. 1895-1904.

DeHon, A., "DPGA Utilization and Application," MIT Artificial Intelligence Laboratory, Proceedings of the Fourth International ACM Symposium on Field-Programmable Gate Arrays (FPGA '96), IEEE Computer Society, pp. 1-7.

Hartenstein, R., "Coarse grain reconfigurable architectures," Design Automation Conference, 2001, Proceedings of the ASP-DAC 2001 Asia and South Pacific, Jan. 30- Feb. 2, 2001, IEEE Jan. 30, 2001, pp. 564-569.

Hastie et al.,"The implementation of hardware subroutines on field programmable gate arrays," Custom Integrated Circuits Conference, 1990, Proceedings of the IEEE 1990, May 16, 1990, pp. 31.3.1 - 31.4.3 (3 pages).

Kastrup, B., "Automatic Hardware Synthesis for a Hybrid Reconfigurable CPU Featuring Philips CPLDs," Proceedings of the PACT Workshop on Reconfigurable Computing, 1998, pp. 5-10.

Koren et al., "A data-driven VLSI array for arbitrary algorithms," IEEE Computer Society, Long Beach, CA vol. 21, No. 10, Oct. 1, 1988, pp. 30-34.

Ling, X., "WASMII: An MPLD with Data-Driven Control on a Virtual Hardware," Journal of Supercomputing, Kluwer Acdemic Publishers, Dordrecht, Netherlands, 1995, pp. 253-276.

Ling et al., "WASMII: A Multifunction Programmable Logic Device (MPLD) with Data Driven Control," The Transactions of the Institute of Electronics, Information and Communication Engineers, Apr. 25, 1994, vol. J77-D-1, Nr. 4, pp. 309-317. [This references is in Chinese, but should be comparable in content to the Ling et al. reference above].

Razdan et al., A High-Performance Microarchitecture with Hardware-Programmable Functional Units, Micro-27, Proceedings of the $27^{th}$ Annual International Symposium on Microarchitecture, IEEE Computer Society and Association for Computing Machinery, Nov. 30-Dec. 2, 1994, pp. 172-180.

Shirazi, et al., "Quantitative analysis of floating point arithmetic on FPGA based custom computing machines," IEEE Symposium on FPGAs for Custom Computing Machines, *IEEE Computer Society Press*, Apr. 19-21, 1995, pp. 155-162.

Siemers et al., "The >S<puter: A Novel Micoarchitecture Mode for Execution inside Superscalar and VLIW Processors Using Reconfigurable Hardware," Australian Computer Science Communications, vol. 20, No. 4, Computer Architecture, Proceedings of the $3^{rd}$ Australian Computer Architecture Conference, Perth, John Morris, Ed., Feb. 2-3, 1998, pp. 169-178.

Skokan, Z.E., "Programmable logic machine (A programmable cell array)," IEEE Journal of Solid-State Circuits, vol. 18, Issue 5, Oct. 1983, pp. 572-578.

Sucyoshi, T, "Present Status and Problems of the Reconfigurable Computing Systems Toward the Computer Evolution," Department of Artificial Intelligence, Kyushi Institute of Technology, Fukuoka, Japan; Institute of Electronics, Information and Communication Engineers, vol. 96, No, 426, IEICE Technical Report (1996), pp. 111-119 [English Abstract Only].

The XPP White Paper, Release 2.1, PACT - A Technical Perspective, Mar. 27, 2002, pp. 1-27.

Weinhardt, M., "Compilation Methods for Structure-programmable Computers," dissertation, ISBN 3-89722-011-3, 1997. [Table of Contents and English Abstract Provided].

Weinhardt, Markus et al., "Pipeline Vectorization," IEEE Transactions on Computer-Aided Design of Integrated Circuits and Systems, vol. 20, No. 2, Feb. 2001, pp. 234-248.

Yeung, A. et al., "A data-driven architecture for rapid prototyping of high throughput DSP algorithms," Dept. of Electrical Engineering and Computer Sciences, Univ. of California, Berkeley, USA, *Proceedings VLSI Signal Processing Workshop, IEEE Press*, pp. 225-234, Napa, Oct. 1992.

Yeung, A. et al., "A reconfigurable data-driven multiprocessor architecture for rapid prototyping of high throughput DSP algorithms," Dept. of Electrical Engineering and Computer Sciences, Univ. of California, Berkeley, USA, pp. 169-178, *IEEE* 1993.

Zhang, et al., Architectural Evaluation of Flexible Digital Signal Processing for Wireless Receivers, Signals, Systems and Computers, 2000; Conference Record of the Thirty-Fourth Asilomar Conference, Bd. 1, Oct. 29, 2000, pp. 78-83.

* cited by examiner

TREATMENT DELIVERY OPTIMIZATION

TECHNICAL FIELD

This invention relates to the field of radiation treatment and, in particular, to optimization of treatment delivery.

BACKGROUND

Pathological anatomies such as tumors and lesions can be treated with an invasive procedure, such as surgery, which can be harmful and full of risks for the patient. A non-invasive method to treat a pathological anatomy or other target is external beam radiation therapy. A "target" as discussed herein may be an anatomical feature(s) of a patient such as a pathological anatomy (e.g., tumor, lesion, vascular malformation, nerve disorder, etc.) or normal anatomy and may include one or more non-anatomical reference structures. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to include radiosurgery and/or radiotherapy unless otherwise noted.

Conventional radiation treatment can be divided into at least two distinct phases: treatment planning and treatment delivery. A treatment planning system may be employed to develop a treatment plan to deliver a requisite dose to a target region, while minimizing exposure to healthy tissue and avoiding sensitive critical structures. A treatment delivery system may be employed to deliver the radiation treatment according to the treatment plan. Treatment plans specify quantities such as the directions and intensities of the applied radiation beams, and the durations of the beam exposure. A treatment plan may be generated from input parameters such as beam positions, beam orientations, beam shapes, beam intensities, and radiation dose distributions (which are typically deemed appropriate by the radiologist in order to achieve a particular clinical goal). Sophisticated treatment plans may be developed using advanced modeling techniques and optimization algorithms.

Two kinds of treatment planning procedures are conventionally known: forward planning and inverse planning. In forward treatment planning, a medical physicist determines the radiation dose of a chosen beam and then calculates how much radiation will be absorbed by the tumor, critical structures (i.e., vital organs), and other healthy tissue. There is no independent control of the dose levels to the tumor and other structures for a given number of beams, because the radiation absorption in a volume of tissue is determined by the properties of the tissue and the distance of each point in the volume to the origin of the beam and the beam axis. The treatment planning system then calculates the resulting dose distribution and the medical physicist may iteratively adjust the values of the treatment parameters during treatment planning until an adequate dose distribution is achieved.

In contrast, the medical physicist may employ inverse planning to specify the minimum dose to the tumor and the maximum dose to other healthy tissues independently, and the treatment planning system then selects the direction, distance, and total number and intensity of the beams in order to achieve the specified dose conditions. Given a desired dose distribution specified and input by the user (e.g., the minimum and maximum doses), the inverse planning module selects and optimizes dose weights and/or beam directions, i.e. select an optimum set of beams that results in such a distribution. Inverse planning may have the advantage of being able to produce better plans, when used by less sophisticated users.

Developing an appropriate treatment plan is especially challenging for tumors that are larger, have irregular shapes, or are close to a sensitive or critical structure. Some conventional radiation systems attempt to optimize the treatment plan prior to delivery. One such radiation system is the TomoTherapy Hi-Art System® available from TomoTherapy, Inc., of Madison, Wis. The Hi-Art System facilitates optimization of the treatment plan by calculating a planned dose into a phantom and then measuring a dose delivered into the phantom. Although such a system may facilitate optimization of the treatment plan during the treatment planning stage, it does not optimize radiation treatment based on the radiation actually delivered to the target region during the treatment delivery stage.

Whether forward planning or inverse planning is used, conventional treatment plans assume specific treatment conditions. However, the actual treatment conditions during treatment delivery are typically different from the treatment planning assumptions. Such differences are not reflected in the treatment plan because they are unknown at the time of treatment planning and may result in an error between the planned radiation dose and the actual radiation dose. Conventional radiation treatment systems allow such deviations as acceptable tolerance errors and do not determine or generate any kind of record of the error. Furthermore, conventional radiation treatment systems do not allow the treatment delivery to be modified based on the difference between the planned dose and the actual dose delivered.

BRIEF DESCRIPTION OF THE DRAWINGS

The present invention is illustrated by way of example, and not by way of limitation, in the figures of the accompanying drawings.

DETAILED DESCRIPTION

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

The following description relates to optimized radiation treatment delivery. A treatment plan is based on certain assumptions regarding the potential conditions during treatment delivery. However, the actual conditions during treatment delivery may be different from those assumptions. In one embodiment, the method described herein tracks the position of the tumor during treatment delivery and calculates an actual dose delivered during treatment delivery, taking into account tumor and intervening tissue movement during treatment. During a treatment session, the radiation delivered in subsequent treatment positions may be adjusted to optimize the actual radiation delivered relative to the treatment plan. Such optimization may occur within a specified threshold. In certain embodiments, the optimization may be done during the current treatment, immediately following the current treatment, or during a subsequent fraction. In one embodiment, an operator may decide to augment the current treatment with additional treatment positions to optimize the treatment delivery so that the actual dose delivered is closer to the calculated dose used to develop the treatment plan. In another embodiment, the operator may receive real-time feedback of these recommended dose adjustments during treatment and at the end of treatment. If the operator decides to implement changes to the treatment, the operator may change the dose at a node, add a node, cancel a node, or terminate the treatment session. In a further embodiment, the treatment delivery may be optimized relative to a single treatment delivery condition, rather than specifically to the actual dose delivered.

Figure 1:
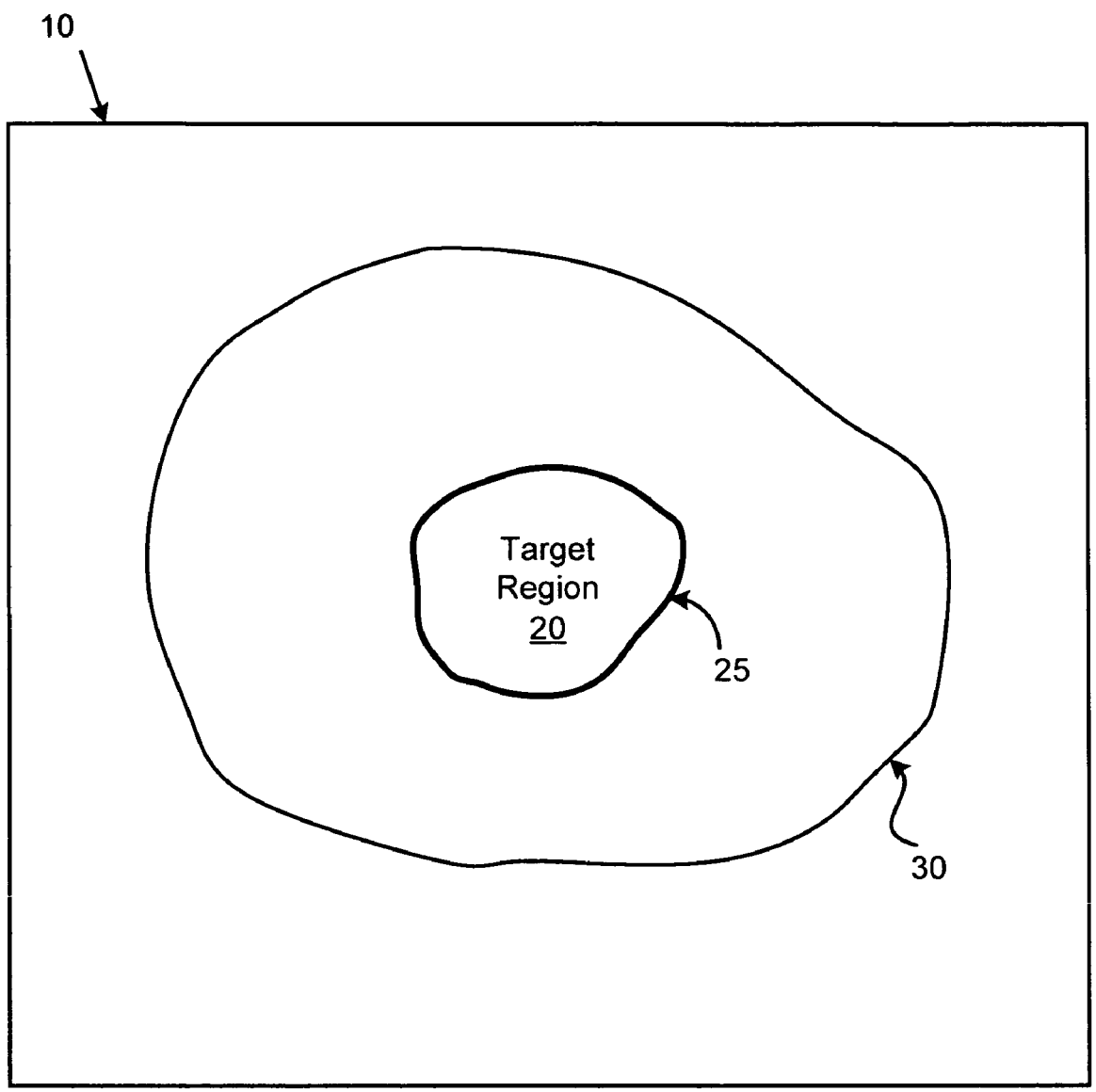
FIG. 1 illustrates a graphical representation of one embodiment of a radiation treatment display showing a target region.

FIG. 1 illustrates a graphical representation of one embodiment of a radiation treatment display 10 showing a target region 20. The displayed image may be a slice of a computed tomography (CT) image or an image obtained using another modality (e.g., magnetic resonance (MR), positron emission tomography (PET), etc.). In one embodiment, the target region 20 is a tumor. Alternatively, the target region may be another pathological anatomy. In other embodiments, the radiation treatment display 10 also may show the relative location of surrounding soft tissues or critical structures. Some examples of critical structures include vital organs, bones, and other physical structures that may be affected by radiation treatment.

Treatment planning software enables the generation of a target region contour 25 around the target region 20. The target region contour 25 may be delineated manually or through an automated process. The task of delineating the target region contour 25 may be complex due to the three-dimensional nature and irregularities of the pathological and normal anatomies, as well as the potentially limited number of beam positions available from the radiation beam source. Based on a specified minimum dose to the target region 20 and the maximum dose to nearby critical structures, the treatment planning software generates a dose isocontour 30 for the target region 20. The dose isocontour 30 represents a given dose percentage (e.g., 60%, 70%, 80%, etc.) of a specified prescription dose for the target region 20. In one embodiment, the dose isocontour 30 matches the target region contour 25 of the target region 20. In other embodiments, the dose isocontour 30 generated by the treatment planning software partially mismatches the target region contour 25 and may include portions of the surrounding tissue or critical structures.

Two principal considerations for an effective radiation treatment system are homogeneity and conformality. Homogeneity is the uniformity of the radiation dose over the volume of the target (e.g., pathological anatomy such as a tumor, lesion, vascular malformation, etc.) and is characterized by a dose volume histogram (DVH). An ideal DVH for a target region 20 would deliver 100 percent of the radiation dose over the volume of the target region 20 and zero radiation elsewhere. Conversely, a DVH for a critical structure delivers as little of the radiation dose as possible to the critical structures.

Conformality is the degree to which the radiation dose matches (conforms) to the shape and extent of the target region 20 (e.g., tumor) in order to avoid damage to adjacent critical structures. More specifically, conformality is a measure of the amount of prescription (Rx) dose (amount of dose applied) within a target region 20, also referred to as a volume of interest (VOI). Conformality may be measured using a conformality index (CI)=total volume at >=Rx dose/target volume at >=Rx dose. Perfect conformality results in a CI=1. With conventional radiotherapy treatment, using treatment planning software, a clinician identifies a dose isocontour for a corresponding VOI for application of a treatment dose (e.g., 3000 cGy).

Figure 2:
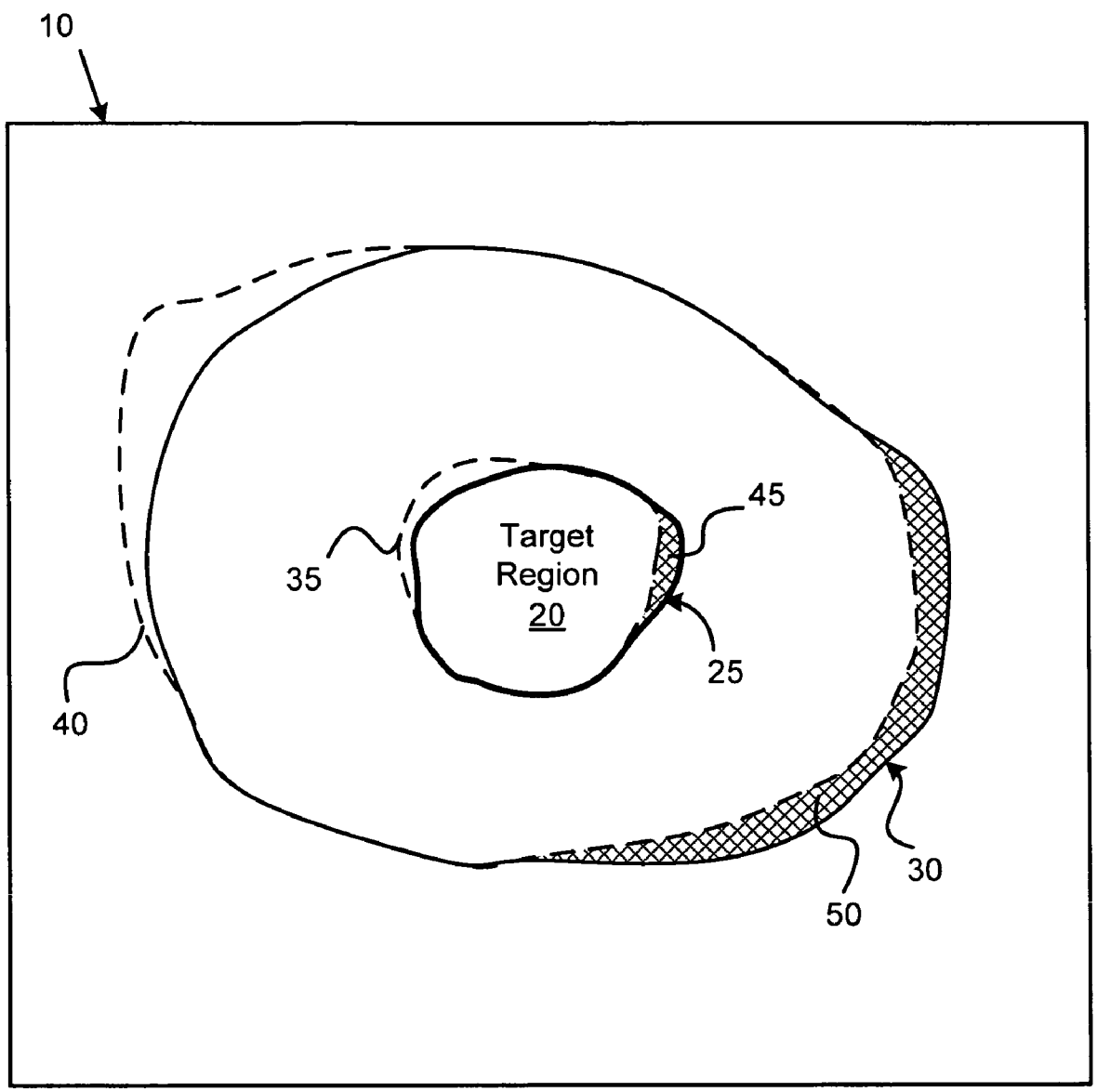
FIG. 2 illustrates a graphical representation of the radiation treatment display showing actual dose isocontours.

FIG. 2 illustrates a graphical representation of the radiation treatment display 10 showing actual dose isocontours 35 and 40. The first actual dose isocontour 35 (shown dashed) is superimposed relative to the target region contour 25. The second actual dose isocontour 40 (shown dashed) is superimposed relative to the planning dose isocontour 30. The difference 45 (shown shaded) between the target region contour 25 and the first actual dose isocontour 35 represents the area within the target region contour 25 that received less than the planned radiation dose. Similarly, the difference 50 (shown shaded) between the planned dose isocontour 30 and the second actual dose isocontour 40 represents the area within the planned dose isocontour 30 that received less then the planned radiation dose. In this way, the radiation treatment display 10 may graphically illustrate the underdosage regions 45 and 50 based on the difference between the planned dose and the dose that is actually delivered.

Figure 3:
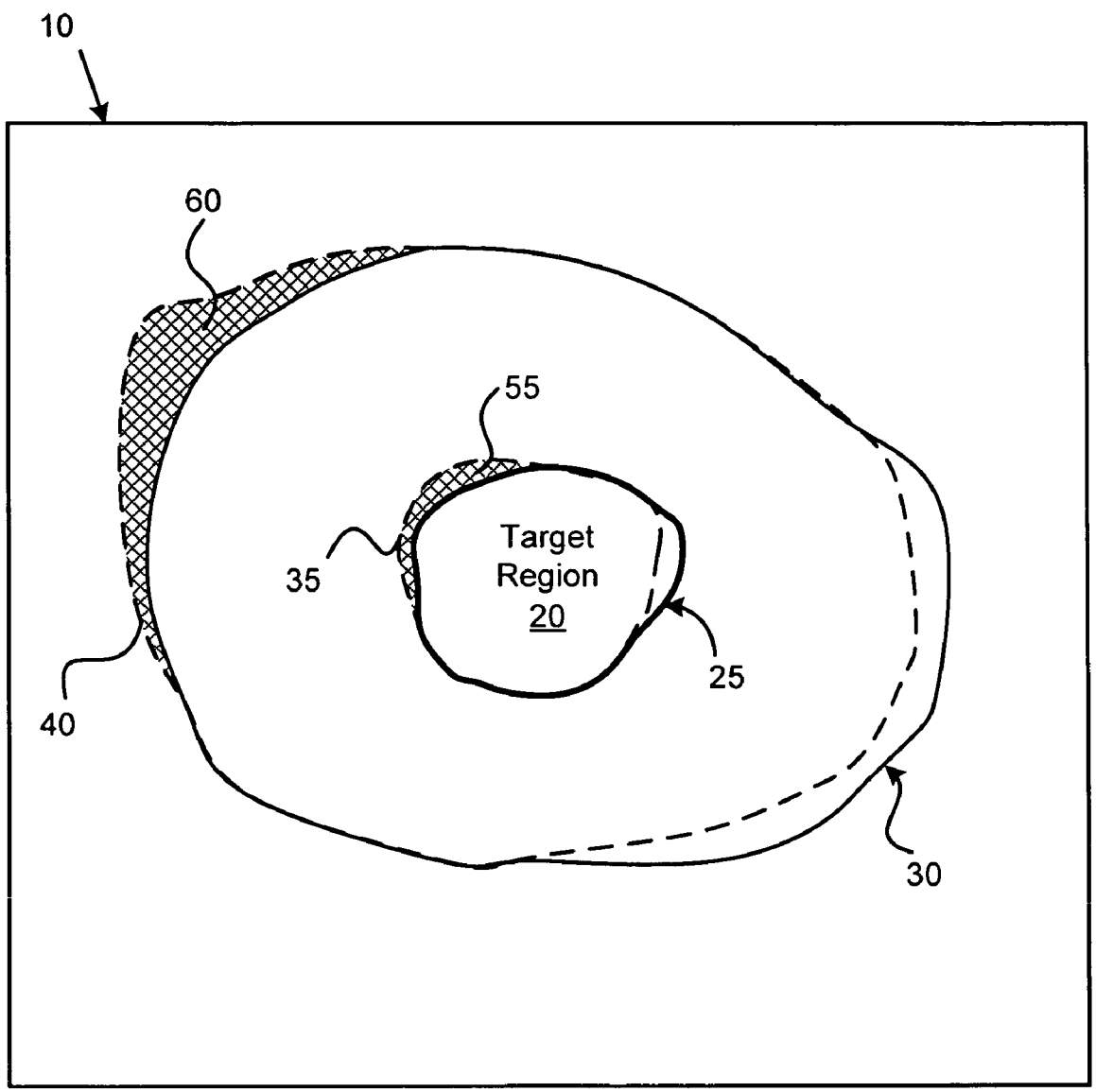
FIG. 3 illustrates another graphical representation of the radiation treatment display showing actual dose isocontours.

FIG. 3 illustrates another graphical representation of the radiation treatment display 10 showing actual dose isocontours 35 and 40. Similar to FIG. 2, the first actual dose isocontour 35 (shown dashed) is overlaid relative to the target region contour 25 and the second actual dose isocontour 40

(shown dashed) is overlaid relative to the planning dose isocontour 30. FIG. 3, however, graphically illustrates the overdosage regions 55 and 60, rather than the underdosage regions 45 and 50 shown in FIG. 2. The difference 55 (shown shaded) between the target region contour 25 and the first actual dose isocontour 35 represents the area outside of the target region contour 25 that received more than the planned radiation dose. Similarly, the difference 50 (shown shaded) between the planned dose isocontour 30 and the second actual dose isocontour 40 represents the portion area outside of the planned dose isocontour 30 that received less then the planned radiation dose. In this way, the radiation treatment display 10 may graphically illustrate the overdosage regions 55 and 60 based on the difference between the planned dose and the dose that is actually delivered.

In one embodiment, treatment delivery software or other system components facilitate determining the actual dose isocontours 35 and 40, based on one or more treatment delivery conditions. Treatment delivery conditions refer generally to factors that may influence the delivery of the radiation treatment, and are divided into two categories: delivery parameters and external factors. Delivery parameters are factors controlled by or subject to the treatment delivery system. Exemplary delivery parameters that influence the actual dosage delivered to a target region 20 may include, but are not limited to, calibration tolerances, beam positions, beam orientations, beam shapes, beam intensity, beam status, attenuation of absorption of intervening tissues and structures, and so forth. External factors, or other factors, are external to the treatment delivery system. Exemplary external factors that may influence the actual dosage delivered to a target region 20 include, but are not limited to, ambient temperature, humidity, air pressure, and so forth.

In general, the total dose delivered to the target region 20 is the sum of the combined dose resultant from each of the radiation treatment beams. In one embodiment, a dose calculation for a single radiation beam may be defined by the following equation:

$$\text{dose}(x) = MU \times TMR(x) \times OP \times OCR(x) \times \left(\frac{800}{SAD(x)}\right)^2,$$

in which dose(x) is measured in cGy, a standard unit of radiation dose, and x is a point in space. The variable MU is the number of Monitor Units for the radiation beam. This is linearly related to the amount of time for which the radiation beam is active. The variable TMR(x) is the Tissue Maximum Ratio measured at the point (x). This models the attenuation of the beam due to passing through tissue. In one embodiment, the density values from the CT may be used to give an "effective depth" which determines the amount of attenuation. The variable OP is the Output Factor related to the collimator being used. In one embodiment, it is not spatially variant, but instead models the number of photons per unit time leaving the collimator. The variable OCR(x) is the Off-axis Correction Ratio, which models the radiation intensity in the cross section of the beam. The variable SAD(x) is the Source-Axis Distance. This is the distance from the radiation source to the point (x). This parameter models the inverse-square fall-off of photon count as distance from the radiation source increases. Although one equation is provided for performing a dose calculation, other delivery parameters and/or external factors may influence the dose calculation.

Where a total dose is tallied over time and multiple radiation beams, the total dose for multiple radiation beams may be defined by the following equation:

$$D(x) = \sum_{i=1}^{N} w_i d_i(x),$$

in which D(x) is the total dose (measured in cGy), x is a point in space, i is a specific beam within a beam set, $\{B_i; 1<i<N\}$, where N may be any number (e.g., N=500), $w_i$ is a beam weight for the i-th beam, and $d_i(x)$ is the dose value delivered to x when $w_i$ is set to unity.

Additional details of dose calculation are known in the art; accordingly, a more detailed description is not provided herein. More detailed descriptions of dose calculations may be referenced in, for example, Faiz M. Khan, *The Physics of Radiation Therapy*, 3d, Lippincott Williams & Wilkins 2003, and American Association of Physicists in Medicine, *AAPM Report No. 85: Tissue Inhomogeneity Corrections for Megavoltage Photon Beams*, Wisconsin, Medical Physics Publishing 2004.

In regard to the delivered dose, the above dose calculation may be modified by changing the parameters in the equation above. For example, if the actual movement of the target region is known relative to the radiation beam at a given point in time, the dose may be recalculated using modified inputs for some or all of the variables of the dose calculation equation. As an illustrative example, if the position x changes to x+dx at time $t_0$. Then for all time $t>t_0$, the value OCR(x+dx) may be substituted for OCR(x) in the dose calculation equation. In other embodiments, other variables may be modified in addition to or instead of the off-axis correction ratio to calculate the actual radiation dose delivered to the target region.

By tracking the position of the target region 20 during treatment delivery and comparing the delivered dose to the planned dose, the treatment delivery system may determine if the planned dose is administered to the target region 20 or if excessive doses are administered to surrounding tissue or critical structures. Tracking the position of the target object 20 may be performed in a number of ways. Some exemplary tracking technologies include fiducial tracking, soft-tissue tracking, and skeletal tracking.

In one embodiment, fiducial tracking involves implanting a metal or other similar object into a patient so that an imaging system can determine the location of the fiducial within the patient. For example, a metal fiducial may be implanted within a tumor so that the imaging system can detect the location of the tumor by determining the location of the fiducial.

In one embodiment, soft-tissue tracking involves correlating a real-time or near real-time image with a pre-treatment image. This type of correlation is referred to as registration. As one example, a real-time ultrasound image may be registered with a pre-treatment image (e.g., MR) in order to determine the location or displacement of the soft tissue target with respect to the one or more common reference points. Registration may be performed using techniques known to those of ordinary skill in the art; accordingly, a detailed description of registration is not provided. One reference that describes exemplary registration techniques is Maintz and Viergeverm, *A Survey of Medical Image Registration*, Oxford University Press, 1998. A reference that describes soft-tissue tracking more generally is Taylor and Stoianovici, *Medical Robotics in*

*Computer-Integrated Surgery*, IEEE Transactions on Robotics and Automation, 2003; 19(g):765-81.

In one embodiment, skeletal tracking involves using an imaging system to determine the location of bones within a patient. Skeletal tracking may be similar to fiducial tracking in some ways. Certain embodiments of skeletal tracking may track rigid skeletal structures that do not move during radiation treatment, while other embodiments may track skeletal structures that move relative to a given reference point.

In another embodiment, the treatment delivery system may tally the delivered dose during a single session as each radiation beam is administered. In this way, the treatment delivery system may potentially adjust the current treatment session in response to a determination that more or less radiation should be delivered to the target region 20 or surrounding structures. For example, the treatment delivery system may iteratively adjust the intensity of the radiation beam in subsequent treatment positions to optimize the delivered dose relative to the treatment plan, given the treatment conditions of the current session. One example of modifying a current treatment session is shown and described in more detail with reference to FIG. 4.

Figure 4:
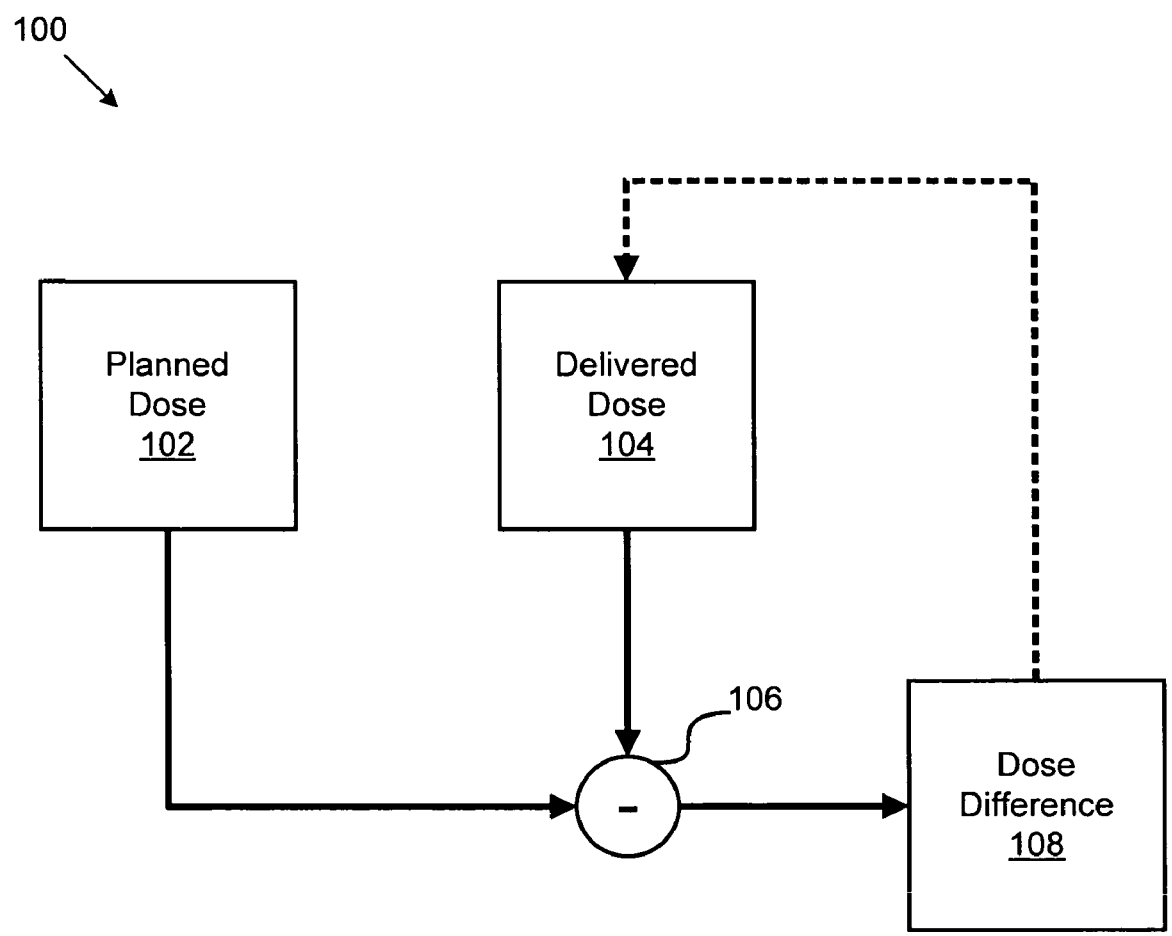
FIG. 4 illustrates a schematic diagram of a treatment delivery process.

FIG. 4 illustrates a schematic diagram of a treatment delivery process 100. The illustrated treatment delivery process 100 represents using the delivered dose 104 to calculate 106 a dose difference 108 and using the dose difference 108 to modify a current treatment session. More specifically, the planned dose 102 from the treatment plan is delivered to the treatment delivery system, which attempts to deliver the planned dose 102. However, the delivered dose 104 may be different from the planned dose 102 due to circumstances during the treatment delivery that might be different from the assumptions used to generate the treatment plan. Therefore, the treatment delivery system calculates the delivered dose 104 based on the actual treatment conditions. For example, the treatment plan may assume that the target region 20 is in a particular location during radiation treatment, but the actual location of the target region 20 during radiation treatment may be different from the planned position. This difference in locations may be determined by tracking the target region 20 during radiation treatment using fiducial, soft-tissue, skeletal, or another tracking technology. Given the difference in locations, the delivered dose 104 to the target region 20 may be more or less than the planned dose 102. Other factors, in addition to location, may affect the actual delivered dose 104. For example, the delivered dose 104 may depend on one or more of the following: air pressure, temperature, humidity, duration that the beam is on, and so forth.

The treatment delivery system uses the planned dose 102 and the delivered dose 104 to generate 106 a dose difference 108, which represents the difference between the planned dose 102 and the delivered dose 104. In one embodiment, the dose difference 108 may be zero for a given beam or set of beams where the radiation that is actually delivered is the same as the radiation specified in the treatment plan. In another embodiment, the dose difference 108 may specify areas of underdosage or overdosage or both compared to the treatment plan. The dose difference 108 may be used (shown by the dashed arrow) in determining the delivery parameters of one or more subsequent radiation beams in the current treatment session. In one embodiment, the comparison between the treatment plan and the actual treatment delivery may occur with each radiation beam. In another embodiment, the comparison between the treatment plan and the actual treatment delivery may result in a cumulative dose difference 108, taking into account any resulting adjustments to the actual radiation delivered to the target region 10 or the surrounding soft tissue and critical structures.

In one embodiment, using the dose difference 108 to determine a delivery parameter of a subsequent radiation beam may be an operation within a process to generate and implement a treatment delivery modification. A treatment delivery modification may be generated based on a previous treatment plan or may be independently generated. More generally, the treatment delivery system may generate a treatment delivery modification based on any actual delivery condition that differs from a condition assumed in the treatment plan. For example, if the treatment plan generated during the treatment planning phase uses an assumption that the beam will be on for a given duration, but the beam is actually on for a shorter period of time, then the treatment delivery system may generate and implement a treatment delivery modification during the treatment delivery phase that compensates for the underdosage in subsequent radiation delivery portions.

In another embodiment, the treatment delivery system may modify a subsequent treatment session rather than the current treatment session. One example of modifying a subsequent treatment session is shown and described in more detail with reference to FIG. 5.

Figure 5:
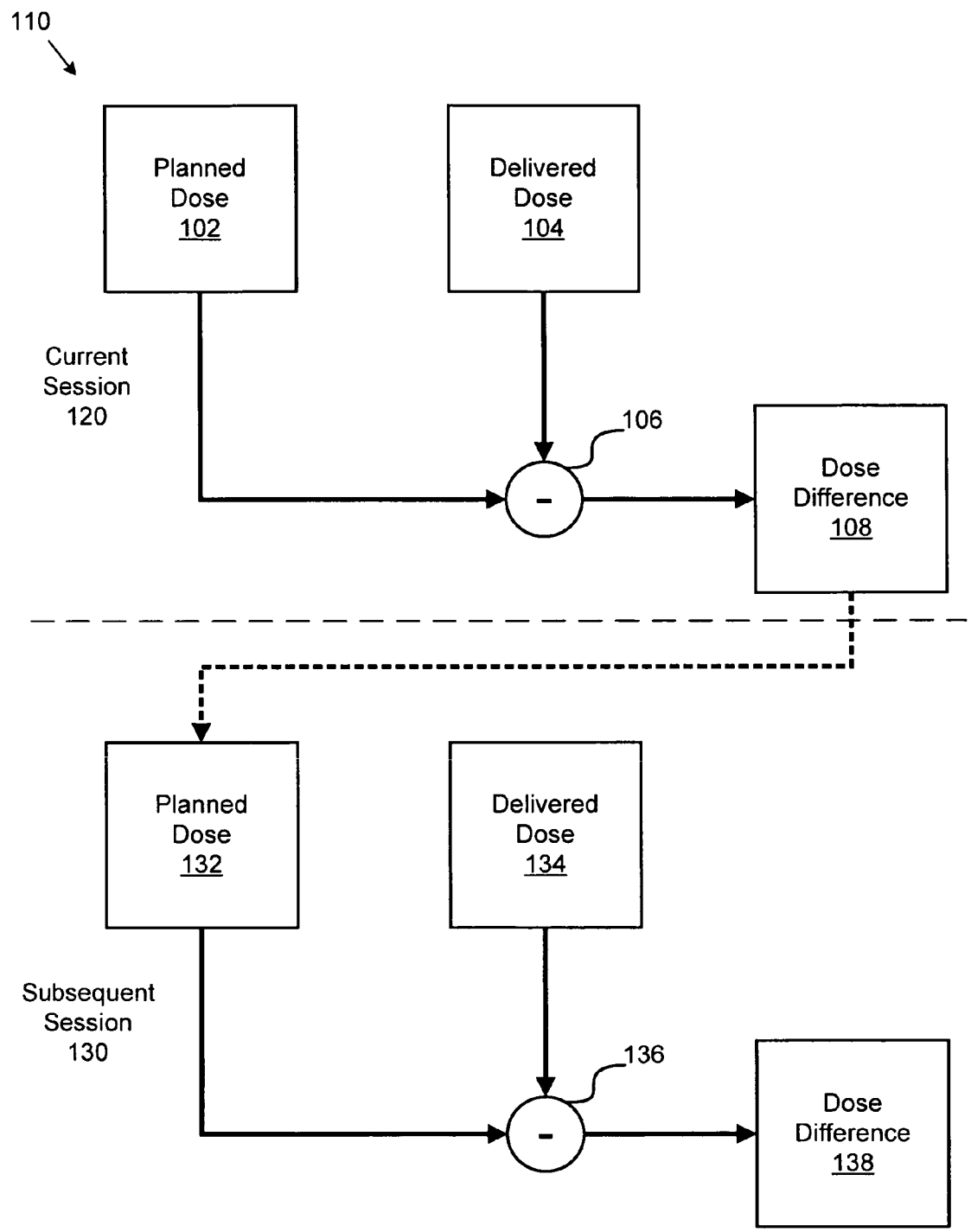
FIG. 5 illustrates a schematic diagram of an alternative treatment delivery process.

FIG. 5 illustrates a schematic diagram of an alternative treatment delivery process 110. The illustrated treatment delivery process 110 represents using the delivered dose 104 to calculate 106 a dose difference 108 of a current session 120 and using the dose difference 108 to modify a subsequent treatment session 130. As depicted in FIG. 5, the current treatment session 120 is represented above the dashed line and the subsequent treatment session 130 is represented below the dashed line. More specifically, the planned dose 102 from the treatment plan is delivered to the treatment delivery system, which attempts to deliver the planned dose 102. However, the delivered dose 104 may be different from the planned dose 102 due to circumstances during the treatment delivery that might be different from the assumptions used to generate the treatment plan. Therefore, the treatment delivery system calculates the delivered dose 104 based on the actual treatment conditions.

The treatment delivery system uses the planned dose 102 and the delivered dose 104 to generate 106 a dose difference 108, which represents the difference between the planned dose 102 and the delivered dose 104. The dose difference 108 may be used (shown by the dashed arrow) in determining the delivery parameters of one or more subsequent treatment sessions 130. In one embodiment, the dose difference 108 may be used to modify a treatment plan of a subsequent treatment session, as shown in FIG. 5. In another embodiment, the dose difference 108 may be used to modify a treatment delivery of a subsequent treatment session, in which the dashed arrow would point to the subsequent treatment delivery rather than the subsequent treatment planning. In another embodiment, the dose difference 108 may be used to modify both a current treatment session and a subsequent treatment session. In another embodiment, the treatment delivery system may present real-time feedback to an operator who may authorize modifications to the current treatment session or to a subsequent treatment session.

Figure 6A:
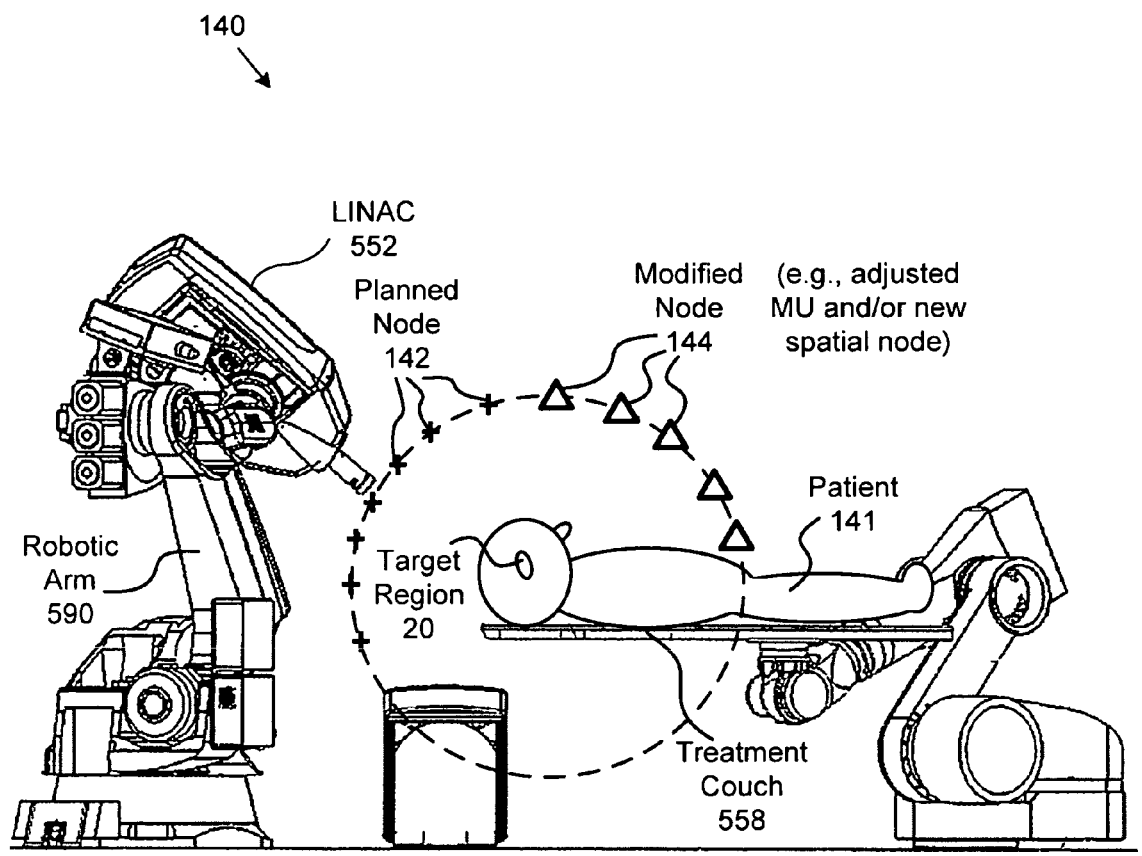
FIG. 6A illustrates a schematic diagram of one embodiment of an optimized node set.

FIG. 6A illustrates a schematic diagram of one embodiment of an optimized node set 140. In general, a node set is a collection of spatial nodes at which a radiation source (e.g., LINAC 552) may be physically located to apply radiation to a target region 20 within a patient 141. The spatial nodes (node set) and associated safe paths interconnecting these spatial nodes is called a workspace. Different types of workspaces may be created and defined during treatment planning for different patient work areas. For example, a workspace may be spherical and defined for treating a target region 20 within a patient's head. Alternatively, a workspace may have other geometries (e.g., elliptical) and defined for treating a target region 20 within another area of the patient 141. Additionally, multiple workspaces may be defined for different portions of a patient 141, each having different radius or source to axis distances ("SAD"), for example, 650 mm and 800 mm. The SAD is the distance between, for example, a collimator lens in a radiation source and the target region 20.

Spatial nodes are located on the surface of workspace. The spatial nodes represent positions where the radiation source 552 may stop during treatment delivery and deliver a dose of radiation to the target region 20 within the patient 141. In one embodiment, a planning node set is defined during treatment planning. The planning node set defines one or more planned nodes 142 that may be used during treatment delivery to position the radiation source 552. Table 1 below presents exemplary values for one embodiment of a planned node set, where each planned node 142 is designated with a letter and assigned a planned MU parameter.

TABLE 1

Planned Node Set

| Node | Type | MU Parameter |
|---|---|---|
| A | PLANNED | 17.2 |
| B | PLANNED | 28.6 |
| C | PLANNED | 19.6 |
| D | PLANNED | 43.8 |
| E | PLANNED | 11.7 |
| F | PLANNED | 11.9 |
| G | PLANNED | 0 |
| H | PLANNED | 21.2 |
| I | PLANNED | 13.4 |
| J | PLANNED | 0 |
| K | PLANNED | 31.7 |
| L | PLANNED | 24.1 |

Exemplary planned nodes 142 are designated by plus ('+') symbols in FIG. 6A. Each planned node 142 designates a position and orientation of the radiation source 552, as well as an MU parameter to deliver a planned dose to the target region 20. In one embodiment, the MU parameter includes a time duration to define how long the radiation beam is on at the corresponding planned node 142 since the MU is linearly related to the time that that the radiation beam is active, as described above. In another embodiment, other parameters may be associated with the planned nodes 142.

During treatment delivery, the robotic arm 590 moves the LINAC 552 to each planned node 142. Even if a particular treatment plan does not call for delivery of a dose of radiation from a particular spatial node, the LINAC 552 still may visit that particular spatial node. In one embodiment, the LINAC 552 may deviate from the planned MU at one or more of the treatment node set and or may deviate from the planned treatment (i.e., the planned node set) in order to deliver a modified radiation dose to the target region 20. For example, a planned node 142 may be discarded and replaced by a modified node 144 at another spatial node of the workspace. In another embodiment, the modified radiation dose may correspond to a change in the amount of time the radiation beam is active at a given node or both. In other embodiments, the modified radiation dose may be implemented by varying one or more other parameters.

In another embodiment, the radiation dose may be modified through variations in the collimator size during treatment, in addition to the MU and the beam direction. For example, modification of a correction dose may be achieved by changing a multi-leaf collimator field geometry and intensity either during treatment or during subsequent fractions. In addition to modifying the radiation field dimensions using a multi-leaf collimator, other embodiments may vary the radiation does by using interposing an attenuation leaf at least partially into radiation beam. In this way, the attenuation leaf may change the intensity of all or part of the radiation beam at the target.

Moreover, in the case of subsequent fractions, the target dose may be set low by some percentage in the initial fractions to avoid an overdose condition which potentially may not be corrected. In other words, planned radiation doses may be set established at a value less than an ideal value because variations in the treatment delivery may cause an overdose compared to the planned dose, and subsequent doses may be unable to compensate for, or correct, such an overdose. Therefore, one embodiment may aggregate plan modifications from one or more previous fractions to optimize dose delivery of a subsequent fraction to the target to minimize or eliminate overdose conditions.

In the illustrated embodiment, the LINAC 552 delivers planned doses at each of a plurality of planned nodes 142. For convenience, the description herein describes the LINAC 552 as moving and applying sequential doses in a clockwise motion along the workspace (dashed circle) surrounding the target region 20 of the patient 141. In other embodiments, the LINAC 552 may move in other directions or apply doses in any order. In parallel, or substantially concurrently with the treatment delivery at the planned nodes 142, the radiation system may calculate one or more delivered doses 104 corresponding to the radiation delivered at the planned nodes 142. The delivered doses 104 may be the same or different from the planned doses 102, as described above.

If the delivered doses (individually and/or in combination) are different from the planned doses 102, then the radiation system may calculate modified doses, which may be substituted for the original planned doses 102 at subsequent modified nodes 144, which are designated by triangles in FIG. 6A. The locations of the modified nodes 144 may be the same as or different than the locations of planned nodes of the treatment plan. Similarly, the radiation applied at the modified nodes 144 may be the same as or different than radiation of the planned doses 102 defined in the treatment plan, for example, by adjusting the MU or on-time of the beam. Table 2 presents exemplary values for one embodiment of the modified node set 140, where the values for planned nodes 142 A through G are the same as in Table 1 above, and the values for planned nodes H through L are replaced with modified nodes 144 generated in response to a determination that the delivered dose 104 at planned nodes 142 A through G is not the same as the planned dose 102 at the same nodes 142. Although MU is used in Table 2 instead of dose for convenience, other embodiments may use dose or another parameter related to dose.

TABLE 2

Modified Node Set

| Node | Type | Planned MU | Delivered MU | Modified MU |
|---|---|---|---|---|
| A | PLANNED | 17.2 | 17.8 | |
| B | PLANNED | 28.6 | 28.2 | |
| C | PLANNED | 19.6 | 22.1 | |
| D | PLANNED | 43.8 | 40.1 | |
| E | PLANNED | 11.7 | 12.1 | |
| F | PLANNED | 11.9 | 12.6 | |

TABLE 2-continued

| | | Modified Node Set | | |
|---|---|---|---|---|
| Node | Type | Planned MU | Delivered MU | Modified MU |
| G | PLANNED | 0 | 0 | |
| H | MODIFIED | 21.2 | | 0.8 |
| I | MODIFIED | 13.4 | | 1.8 |
| J | MODIFIED | 0 | | 3.9 |
| K | MODIFIED | 31.7 | | 6.2 |
| L | MODIFIED | 24.1 | | 2.2 |
| M | MODIFIED | NONE | N/A | 3.1 |

The example shown in Table 2 illustrates one embodiment of delivering modified radiation doses at some of the planned nodes 142 in the radiation treatment plan. In particular, the delivered dose at each of the planned nodes 142 A through G may be determined and compared to the planned doses. In response to determining that the planned and delivered doses are not the same, modified radiation doses may be delivered at the subsequent planned nodes 142H-L. In the example provided, the radiation dose at the planned nodes 142H-L are each increased by a modified dose. However, in other embodiment, the planned doses may be decreases or remain the same. Additionally, new nodes such as the modified node 144M may be added to the radiation treatment delivery.

In another embodiment, the radiation system may implement planned nodes 142 and modified nodes 144 in any order, including alternating, depending at least in part on any dose differences 108 between the planned doses 102 and the delivered doses 104 at one or more spatial nodes. Moreover, the radiation system may present modified doses in a current treatment fraction or in subsequent treatment fractions. For example, the planned doses and delivered doses may be input into inverse planning for subsequent fractions or treatment sessions. Additionally, some embodiments having sufficient processing power may implement dose modifications in real-time during dose delivery at a node. For example, if the radiation beam is planned to be on for one time unit, the radiation system may determine during delivery of the radiation at a given node that the delivered dose is different from the planned dose. In response to such a determination, the radiation system may dynamically modify the radiation dose and complete radiation delivery at the node according to the modified dose.

In a further embodiment, the radiation system may take into account a dynamic motion of the target in calculating the planned and delivered doses. For example, the radiation system may consider rotation, translation, and deformation of the target over time. Rotation refers to rotation of the target about an axis with respect one of the spatial nodes. Translation refers to movement of the target in a direction with respect to one of the spatial nodes. Deformation refers to deformation of the target, e.g., stretching, twisting, etc., with respect to one of the spatial nodes. In one embodiment, the radiation system may develop two-, three-, or four-dimensional models to describe the rotation, translation, or deformation of the target. Alternatively, the radiation system may monitor the rotation, translation, and deformation of the target in real-time. Radiation doses, as well as node locations and delivery times and durations, may be modified to change the radiation dose delivered to the target.

The illustrated optimized node set 140 is implemented via a linear accelerator (LINAC) 552 that is mounted on a robotic arm 590 (embodiments of the LINAC 552 and robotic arm 590 are described in more detail with reference to FIGS. 10 and 11). In alternative embodiments, the optimized node set 140 may be implemented using other technology such as a gantry or other radiation system.

Figure 6B:
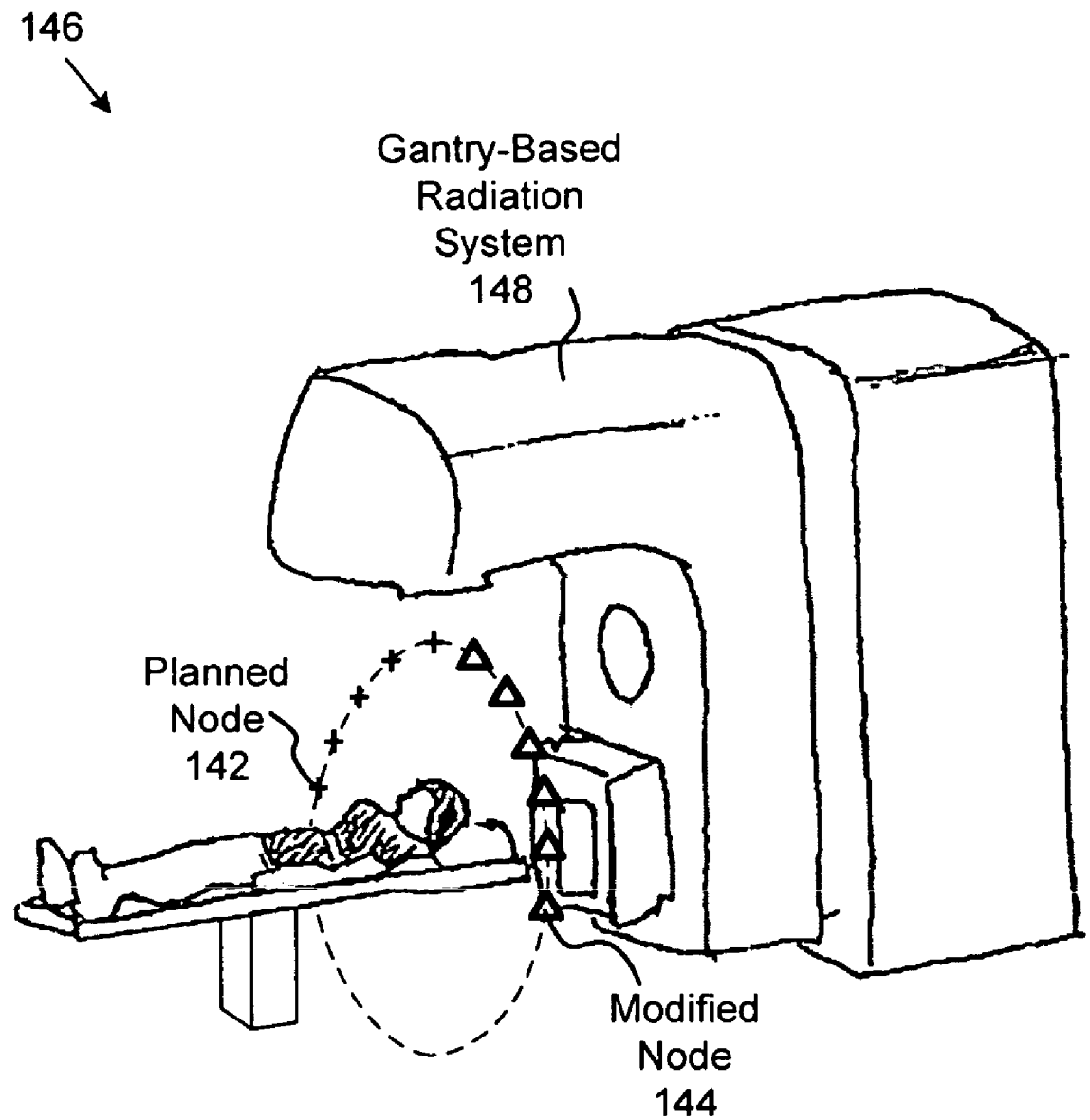
FIG. 6B illustrates a schematic diagram of another embodiment of an optimized node set.

FIG. 6B illustrates a schematic diagram of another embodiment of an optimized node set 146. In particular, the alternative optimized node set 146 may be delivered by a gantry-based radiation system or any another radiation system that is not a LINAC 552 on a robotic arm 590. Although a specific number of nodes are shown in FIGS. 6A and 6B, other implementations may employ fewer or more nodes. Furthermore, other embodiments may modify more or less nodes and may determine such modification(s) based on arty number of previous nodes individually or in combination. Additionally, modified doses 144 may be determined based on a single delivered dose 104 or a combination of several delivered doses 104, including delivered doses 104 corresponding to planned doses 102, modified doses 144, or both.

Figure 7:
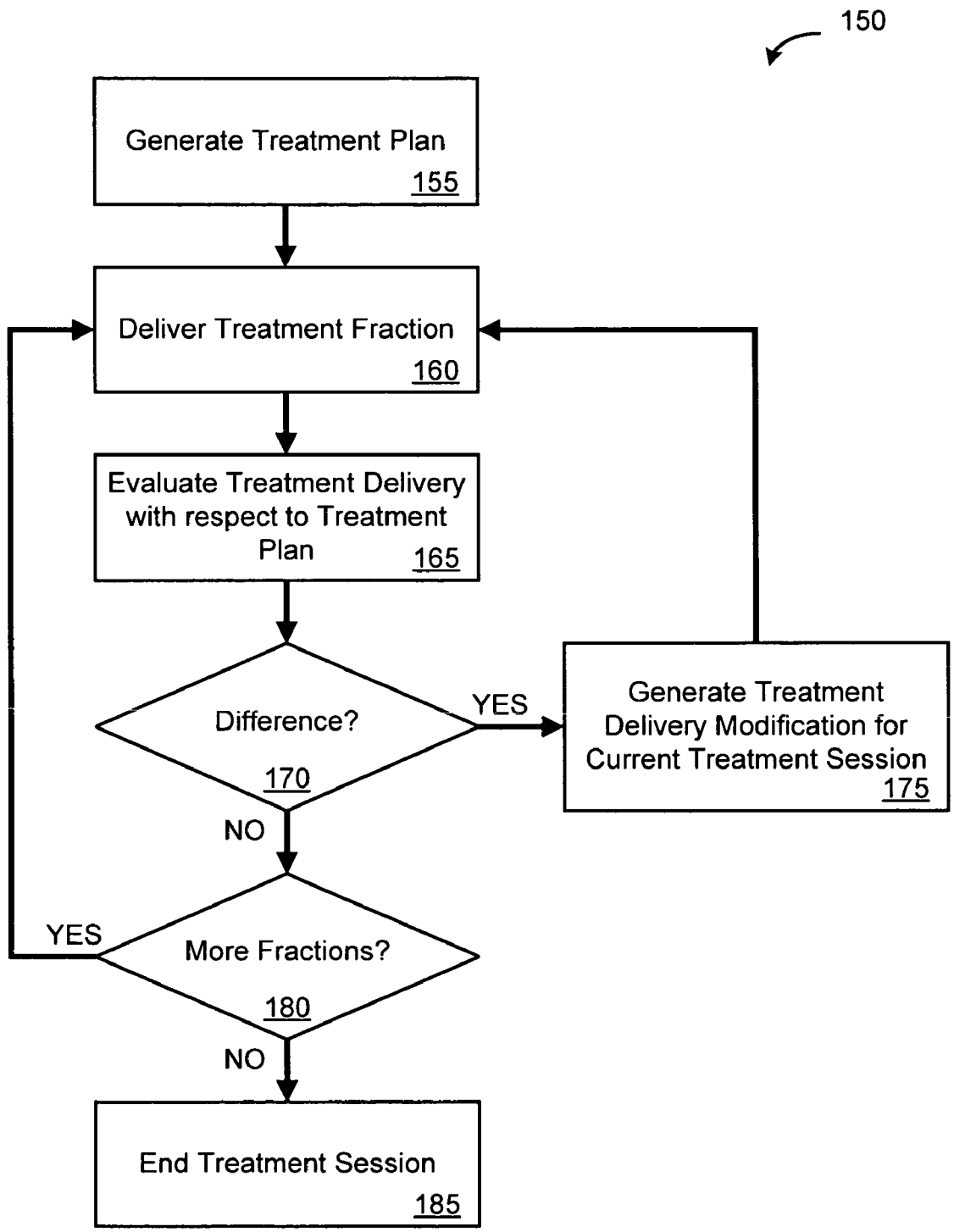
FIG. 7 illustrates a schematic flow chart of a treatment optimization method.

FIG. 7 illustrates a schematic flow chart of a treatment optimization method 150. In one embodiment, the depicted treatment optimization method 150 may be implemented in hardware, software, and/or firmware on a treatment system, such as the treatment system 500 of FIG. 10. Although the treatment optimization method 150 is described in terms of the treatment system 500, or certain parts of the treatment system 500, embodiments the treatment optimization method 150 may be implemented on another system or independent of the treatment system 500.

The illustrated treatment optimization method 150 begins and the treatment planning system generates 155 a treatment plan. In general, the treatment plan indicates certain radiation treatment parameters which are designed to deliver a particular radiation dose to a target region 20 and potentially minimize radiation exposure to surrounding tissue and structures. The treatment delivery system then delivers 160 a fraction of the radiation treatment according to the treatment plan. As used herein, a fraction refers to a portion of a radiation treatment plan. As described above, the actual dose delivered via one or more radiation beams may differ from the treatment plan due to differences between the actual treatment conditions and the treatment plan assumptions.

The treatment delivery system subsequently evaluates 165 the treatment delivery with respect to the treatment plan to determine 170 if there is a difference between the actual treatment conditions and the treatment planning assumptions. The difference, if any, may result in an overdose or an underdose. If there is a difference between the actual treatment conditions and the treatment planning assumptions, then the treatment delivery system generates 175 a treatment delivery modification based on the difference. In one embodiment, the treatment delivery modification may be described in the form of a dose difference. Alternatively, the treatment delivery modification may be described in terms of one or more treatment delivery conditions. The treatment delivery modification may be used in a current treatment session, as depicted in FIG. 4. After the treatment delivery system generates the treatment delivery modification, the treatment delivery system delivers 160 another fraction of the radiation treatment, taking into account the treatment delivery modification. The treatment optimization method 150 continues in this manner until all of the fractions are delivered 180, or until a sufficient number of fractions are delivered according to the cumulative delivered dose and the objectives of the treatment plan. The depicted treatment optimization method 150 then ends.

In another embodiment the treatment optimization method 150 may implement four-dimensional radiation treatment, including using a four-dimensional treatment plan generated using, for example, a four-dimensional CT image. The radiation system may deliver the four-dimensional treatment plan and evaluate treatment delivery with respect to the treatment plan, taking into account four-dimensional tissue movement such as rotation, translation, or deformation. Additionally, the feedback loop of the treatment optimization method 150 may occur relatively quickly in radiation system which are capably of high processing speeds such as parallel processing. In one embodiment, the radiation system may calculate a treatment delivery modification during beam delivery at a particular node and modify the current beam delivery at the same node. Alternatively, the treatment delivery modification may be implemented at one or more subsequent nodes in the current treatment session, or at one or more nodes of a subsequent treatment session.

Figure 8:
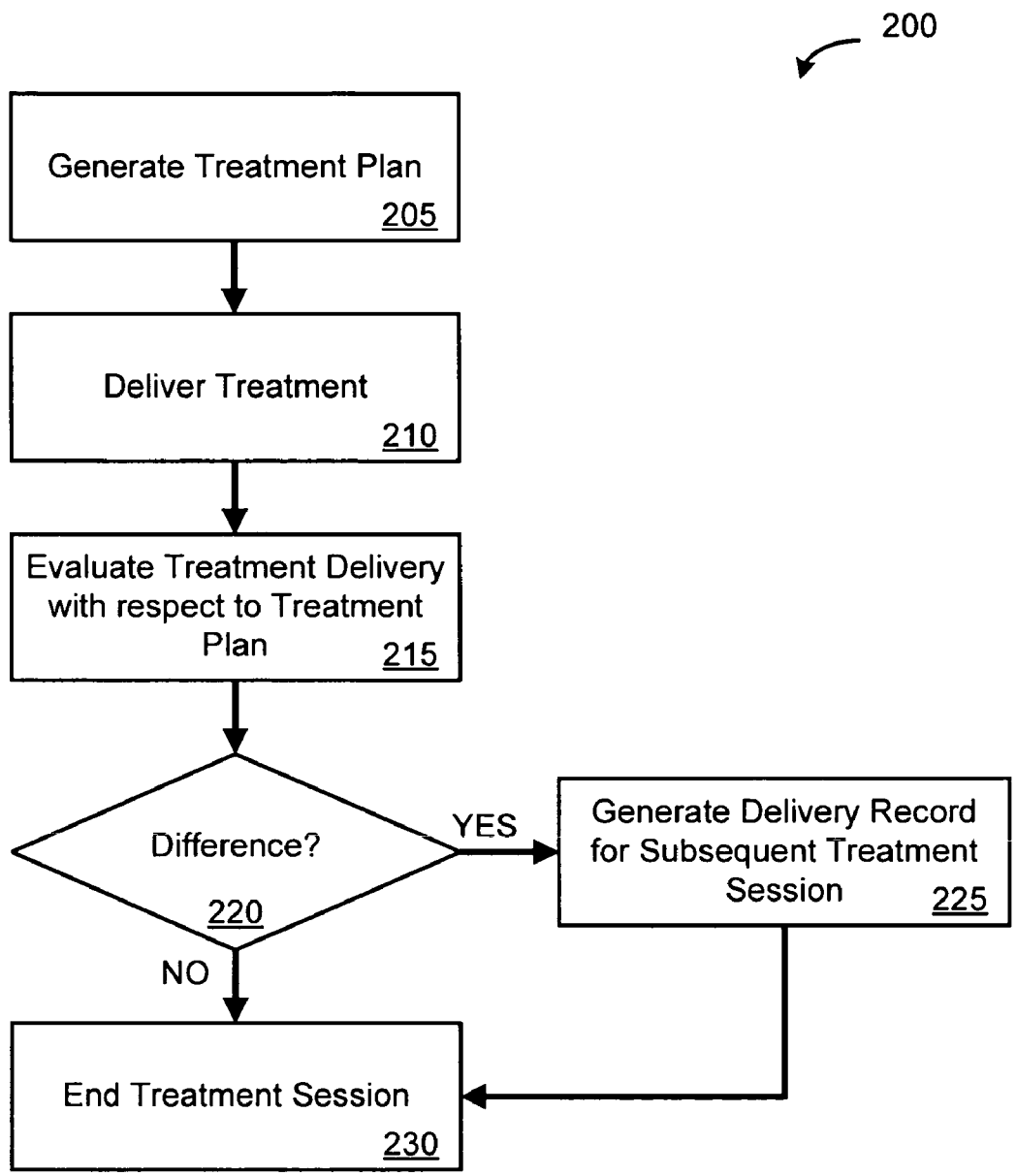
FIG. 8 illustrates a schematic flow chart of an alternative treatment optimization method.

FIG. 8 illustrates a schematic flow chart of an alternative treatment optimization method 200. One difference between the treatment optimization method 150 of FIG. 7 and the alternative treatment optimization method 200 of FIG. 8 is that the alternative treatment optimization method 200 is directed to modifying a subsequent treatment session rather than a current treatment session. In one embodiment, the depicted alternative treatment optimization method 200 may be implemented in hardware, software, and/or firmware on a treatment system, such as the treatment system 500 of FIG. 10. Although the alternative treatment optimization method 200 is described in terms of the treatment system 500, or certain parts of the treatment system 500, embodiments the alternative treatment optimization method 200 may be implemented on another system or independent of the treatment system 500.

The illustrated alternative treatment optimization method 200 begins and the treatment planning system generates 205 a treatment plan. In general, the treatment plan indicates certain radiation treatment parameters which are designed to deliver a particular radiation dose to a target region 20 and potentially minimize radiation exposure to surrounding tissue and structures. The treatment delivery system then delivers 210 the radiation treatment, or a portion thereof, according to the treatment plan. As described above, the actual dose delivered via one or more radiation beams may differ from the treatment plan due to differences between the actual treatment conditions and the treatment plan assumptions.

The treatment delivery system subsequently evaluates 215 the treatment delivery with respect to the treatment plan to determine 220 if there is a difference between the actual treatment conditions and the treatment planning assumptions. The difference, if any, may result in an overdose or an underdose. If there is a difference between the actual treatment conditions and the treatment planning assumptions, then the treatment delivery system generates 225 a record of the difference. The delivery record may be used in a subsequent treatment session, as depicted in FIG. 5. After the treatment delivery system generates the delivery record, or if there are no differences between the actual treatment conditions and the treatment planning assumptions, then the depicted alternative treatment optimization method 200 ends.

Figure 9:
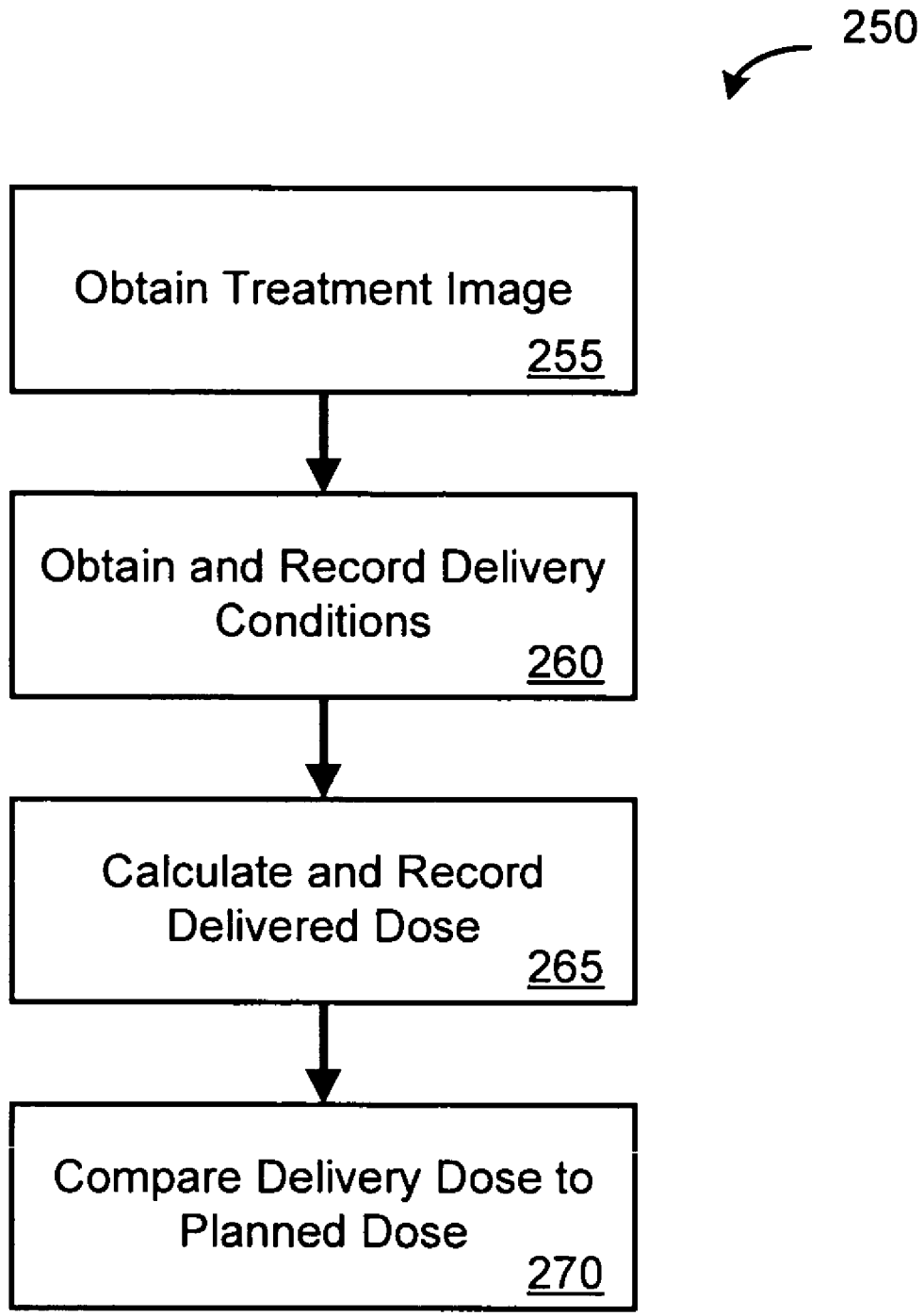
FIG. 9 illustrates a schematic flow chart of a dose comparison method.

FIG. 9 illustrates a schematic flow chart of a dose comparison method 250. In one embodiment, the dose comparison method 250 may be used to facilitate the treatment optimization method 150 of FIG. 7 or the alternative treatment optimization method 200 of FIG. 8. In particular, the dose comparison method 250 may facilitate the evaluation operation 165 of FIG. 5 or the evaluation operation 215 of FIG. 7. The depicted dose comparison method 250 may be implemented in hardware, software, and/or firmware on a treatment system, such as the treatment system 500 of FIG. 10. Although the dose comparison method 250 is described in terms of the treatment system 500, or certain parts of the treatment system 500, embodiments the dose comparison method 250 may be implemented on another system or independent of the treatment system 500.

The illustrated dose comparison method 250 begins and the treatment delivery system obtains 255 a treatment image. In one embodiment, the treatment image is a CT image, or an image from another modality, which allows the treatment delivery system to determine at least one of the treatment delivery conditions. For example, the treatment delivery system may use the treatment image to determine if the target region 20 is in the same position as is assumed in the treatment plan. The treatment delivery system also may obtain 260 and record other treatment delivery conditions such as beam position, beam orientation, beam intensity, ambient temperature, ambient humidity, and so forth. In one embodiment, the treatment delivery system may obtain any of the treatment parameters or external factors. In another embodiment, the illustrated operations of the dose comparison method 250 may be performed in another order or, at least in part, in parallel. For example, the treatment delivery system may obtain 260 and record the treatment delivery conditions prior to or concurrently with obtaining 255 the treatment image.

The treatment delivery system then uses the known treatment delivery conditions to calculate 265 and record the delivered dose. For example, the beam intensity may be calculated relative to a calibrated intensity, given the ambient temperature and humidity, as well as a known correlation between beam intensity, temperature, and humidity. Similarly, the treatment delivery system may calculate how much radiation is actually delivered to certain portions of the target region 20 based on the beam position, beam orientation, and actual location of the target region 20, as indicated by the treatment image. After calculating the delivered dose, the treatment delivery system compares 270 the delivered dose to the planned dose to determine if there is a difference between the delivered dose and the planned dose. The depicted dose comparison method 250 then ends.

Figure 10:
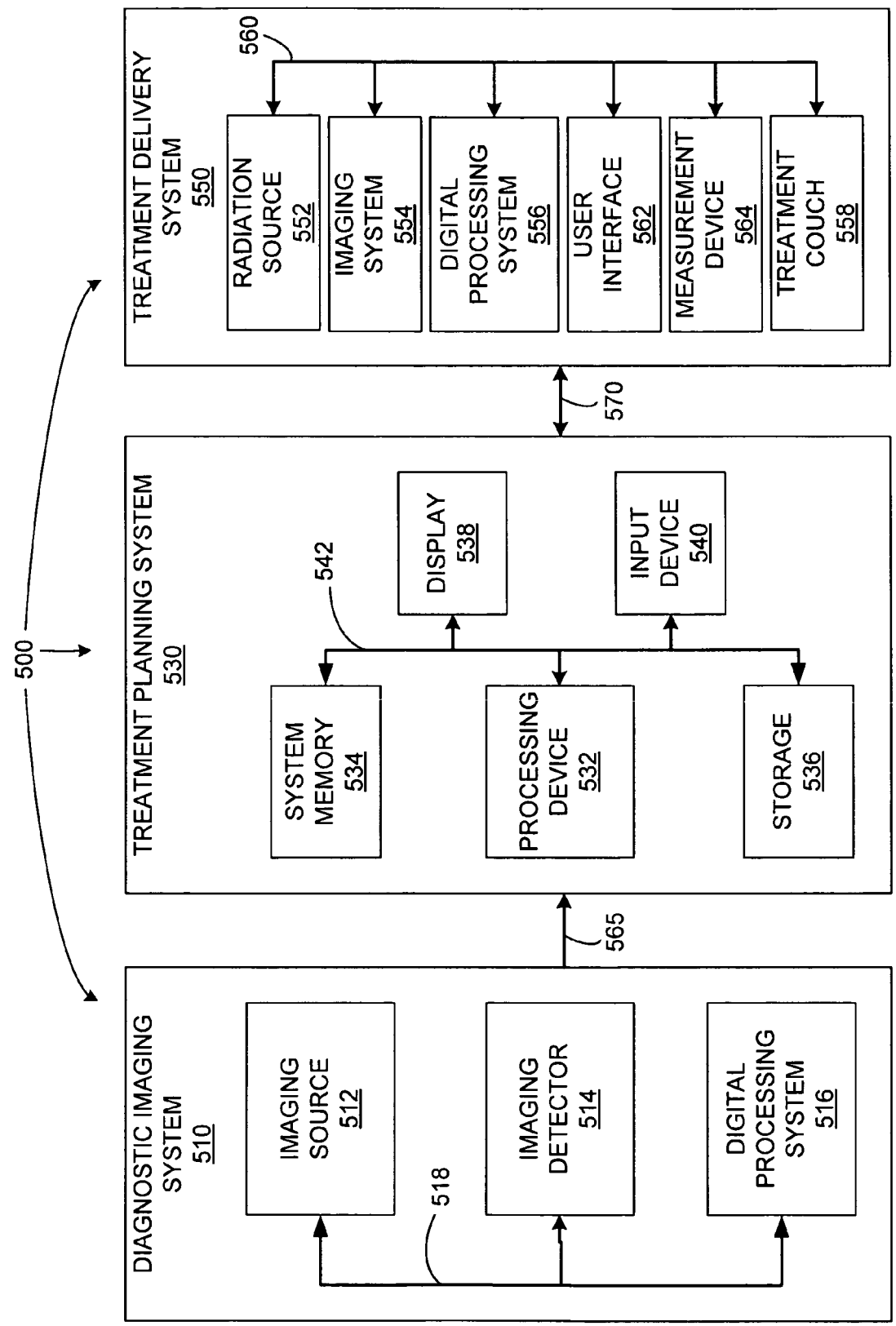
FIG. 10 illustrates one embodiment of a treatment system that may be used to perform radiation treatment in which embodiments of the present invention may be implemented.

FIG. 10 illustrates one embodiment of a treatment system 500 that may be used to perform radiation treatment in which embodiments of the present invention may be implemented. The depicted treatment system 500 includes a diagnostic imaging system 510, a treatment planning system 530, and a treatment delivery system 550. In other embodiments, the treatment system 500 may include fewer or more component systems.

The diagnostic imaging system 510 is representative of any system capable of producing medical diagnostic images of a volume of interest (VOI) in a patient, which images may be used for subsequent medical diagnosis, treatment planning, and/or treatment delivery. For example, the diagnostic imaging system 510 may be a computed tomography (CT) system, a single photon emission computed tomography (SPECT) system, a magnetic resonance imaging (MRI) system, a positron emission tomography (PET) system, a near infrared fluorescence imaging system, an ultrasound system, or another similar imaging system. For ease of discussion, any specific references herein to a particular imaging system such as a CT x-ray imaging system (or another particular system) is representative of the diagnostic imaging system 510, generally, and does not preclude other imaging modalities, unless noted otherwise.

The illustrated diagnostic imaging system 510 includes an imaging source 512, an imaging detector 514, and a digital processing system 516. The imaging source 512, imaging detector 514, and digital processing system 516 are coupled to one another via a communication channel 518 such as a bus. In one embodiment, the imaging source 512 generates an imaging beam (e.g., x-rays, ultrasonic waves, radio frequency waves, etc.) and the imaging detector 514 detects and receives the imaging beam. Alternatively, the imaging detector 514 may detect and receive a secondary imaging beam or an emission stimulated by the imaging beam from the imaging source (e.g., in an MRI or PET scan). In one embodiment, the diagnostic imaging system 510 may include two or more diagnostic imaging sources 512 and two or more corresponding imaging detectors 514. For example, two x-ray sources 512 may be disposed around a patient to be imaged, fixed at an angular separation from each other (e.g., 90 degrees, 45 degrees, etc.) and aimed through the patient toward corresponding imaging detectors 514, which may be diametrically opposed to the imaging sources 514. A single large imaging detector 514, or multiple imaging detectors 514, also may be illuminated by each x-ray imaging source 514. Alternatively, other numbers and configurations of imaging sources 512 and imaging detectors 514 may be used.

The imaging source 512 and the imaging detector 514 are coupled to the digital processing system 516 to control the imaging operations and process image data within the diagnostic imaging system 510. In one embodiment, the digital processing system 516 may communicate with the imaging source 512 and the imaging detector 514. Embodiments of the digital processing system 516 may include one or more general-purpose processors (e.g., a microprocessor), special purpose processors such as a digital signal processor (DSP), or other type of devices such as a controller or field programmable gate array (FPGA). The digital processing system 516 also may include other components (not shown) such as memory, storage devices, network adapters, and the like. In one embodiment, the digital processing system 516 generates digital diagnostic images in a standard format such as the Digital Imaging and Communications in Medicine (DICOM) format. In other embodiments, the digital processing system 516 may generate other standard or non-standard digital image formats.

Additionally, the digital processing system 516 may transmit diagnostic image files such as DICOM files to the treatment planning system 530 over a data link 560. In one embodiment, the data link 560 may be a direct link, a local area network (LAN) link, a wide area network (WAN) link such as the Internet, or another type of data link. Furthermore, the information transferred between the diagnostic imaging system 510 and the treatment planning system 530 may be either pulled or pushed across the data link 560, such as in a remote diagnosis or treatment planning configuration. For example, a user may utilize embodiments of the present invention to remotely diagnose or plan treatments despite the existence of a physical separation between the system user and the patient.

The illustrated treatment planning system 530 includes a processing device 532, a system memory device 534, an electronic data storage device 536, a display device 538, and an input device 540. The processing device 532, system memory 534, storage 536, display 538, and input device 540 may be coupled together by one or more communication channel 542 such as a bus.

The processing device 532 receives and processes image data. The processing device 532 also processes instructions and operations within the treatment planning system 530. In certain embodiments, the processing device 532 may include one or more general-purpose processors (e.g., a microprocessor), special purpose processors such as a digital signal processor (DSP), or other types of devices such as a controller or field programmable gate array (FPGA).

In particular, the processing device 532 may be configured to execute instructions for performing treatment operations discussed herein. For example, the processing device 532 may identify a non-linear path of movement of a target within a patient and develop a non-linear model of the non-linear path of movement. In another embodiment, the processing device 532 may develop the non-linear model based on a plurality of position points and a plurality of direction indicators. In another embodiment, the processing device 532 may generate a plurality of correlation models and select one of the plurality of models to derive a position of the target. Furthermore, the processing device 532 may facilitate other diagnosis, planning, and treatment operations related to the operations described herein.

In one embodiment, the system memory 534 may include random access memory (RAM) or other dynamic storage devices. As described above, the system memory 534 may be coupled to the processing device 532 by the communication channel 542. In one embodiment, the system memory 534 stores information and instructions to be executed by the processing device 532. The system memory 534 also may be used for storing temporary variables or other intermediate information during execution of instructions by the processing device 532. In another embodiment, the system memory 534 also may include a read only memory (ROM) or other static storage device for storing static information and instructions for the processing device 532.

In one embodiment, the storage 536 is representative of one or more mass storage devices (e.g., a magnetic disk drive, tape drive, optical disk drive, etc.) to store information and instructions. The storage 536 and/or the system memory 534 also may be referred to as machine readable media. In a specific embodiment, the storage 536 may store instructions to perform the modeling operations discussed herein. For example, the storage 536 may store instructions to acquire and store data points, acquire and store images, identify non-linear paths, develop linear and/or non-linear correlation models, and so forth. In another embodiment, the storage 536 may include one or more databases.

In one embodiment, the display 538 may be a cathode ray tube (CRT) display, a liquid crystal display (LCD), or another type of display device. The display 538 displays information (e.g., a two-dimensional or three-dimensional representation of the VOI) to a user. The input device 540 may include one or more user interface devices such as a keyboard, mouse, trackball, or similar device. The input device(s) 540 may also be used to communicate directional information, to select commands for the processing device 532, to control cursor movements on the display 538, and so forth.

Although one embodiment of the treatment planning system 530 is described herein, the described treatment planning system 530 is only representative of an exemplary treatment planning system 530. Other embodiments of the treatment planning system 530 may have many different configurations and architectures and may include fewer or more components. For example, other embodiments may include multiple buses, such as a peripheral bus or a dedicated cache bus. Furthermore, the treatment planning system 530 also may include Medical Image Review and Import Tool (MIRIT) to support DICOM import so that images can be fused and targets delineated on different systems and then imported into the treatment planning system 530 for planning and dose calculations. In another embodiment, the treatment planning system 530 also may include expanded image fusion capabilities that allow a user to plan treatments and view dose distributions on any one of various imaging modalities such as MRI, CT, PET, and so forth. Furthermore, the treatment planning system 530 may include one or more features of convention treatment planning systems.

In one embodiment, the treatment planning system 530 may share a database on the storage 536 with the treatment delivery system 550 so that the treatment delivery system 550 may access the database prior to or during treatment delivery. The treatment planning system 530 may be linked to treatment delivery system 550 via a data link 570, which may be a direct link, a LAN link, or a WAN link, as discussed above with respect to data link 560. Where LAN, WAN, or other distributed connections are implemented, any of components of the treatment system 500 may be in decentralized locations so that the individual systems 510, 530 and 550 may be physically remote from one other. Alternatively, some or all of the functional features of the diagnostic imaging system 510, the treatment planning system 530, or the treatment delivery system 550 may be integrated with each other within the treatment system 500.

The illustrated treatment delivery system 550 includes a radiation source 552, an imaging system 554, a digital processing system 556, and a treatment couch 558. The radiation source 552, imaging system 554, digital processing system 556, and treatment couch 558 may be coupled to one another via one or more communication channels 560. One example of a treatment delivery system 550 is shown and described in more detail with reference to FIG. 11.

In one embodiment, the radiation source 552 is a therapeutic or surgical radiation source 552 to administer a prescribed radiation dose to a target volume in conformance with a treatment plan. For example, the target volume may be an internal organ, a tumor, a region. As described above, reference herein to the target, target volume, target region, target area, or internal target refers to any whole or partial organ, tumor, region, or other delineated volume that is the subject of a treatment plan.

In one embodiment, the imaging system 554 of the treatment delivery system 550 captures intra-treatment images of a patient volume, including the target volume, for registration or correlation with the diagnostic images described above in order to position the patient with respect to the radiation source. Similar to the diagnostic imaging system 510, the imaging system 554 of the treatment delivery system 550 may include one or more sources and one or more detectors.

The treatment delivery system 550 also may include a digital processing system 556 to control the radiation source 552, the imaging system 554, and a treatment couch 558, which is representative of any patient support device. The digital processing system 556 may include one or more general-purpose processors (e.g., a microprocessor), special purpose processors such as a digital signal processor (DSP), or other devices such as a controller or field programmable gate array (FPGA). Additionally, the digital processing system 556 may include other components (not shown) such as memory, storage devices, network adapters, and the like.

The illustrated treatment delivery system 550 also includes a user interface 562 and a measurement device 564. In one embodiment, the user interface 562 allows a user to interface with the treatment delivery system 550. In particular, the user interface 562 may include input and output devices such as a keyboard, a display screen, and so forth. In one embodiment, the radiation treatment display 10 of FIGS. 1 through 3 are incorporated into the user interface 562. The measurement device 564 may be one or more devices that measure external factors such as the external factors described above, which may influence the radiation that is actually delivered to the target region 20. Some exemplary measurement devices include a thermometer to measure ambient temperature, a hygrometer to measure humidity, a barometer to measure air pressure, or any other type of measurement device to measure an external factor.

Figure 11:
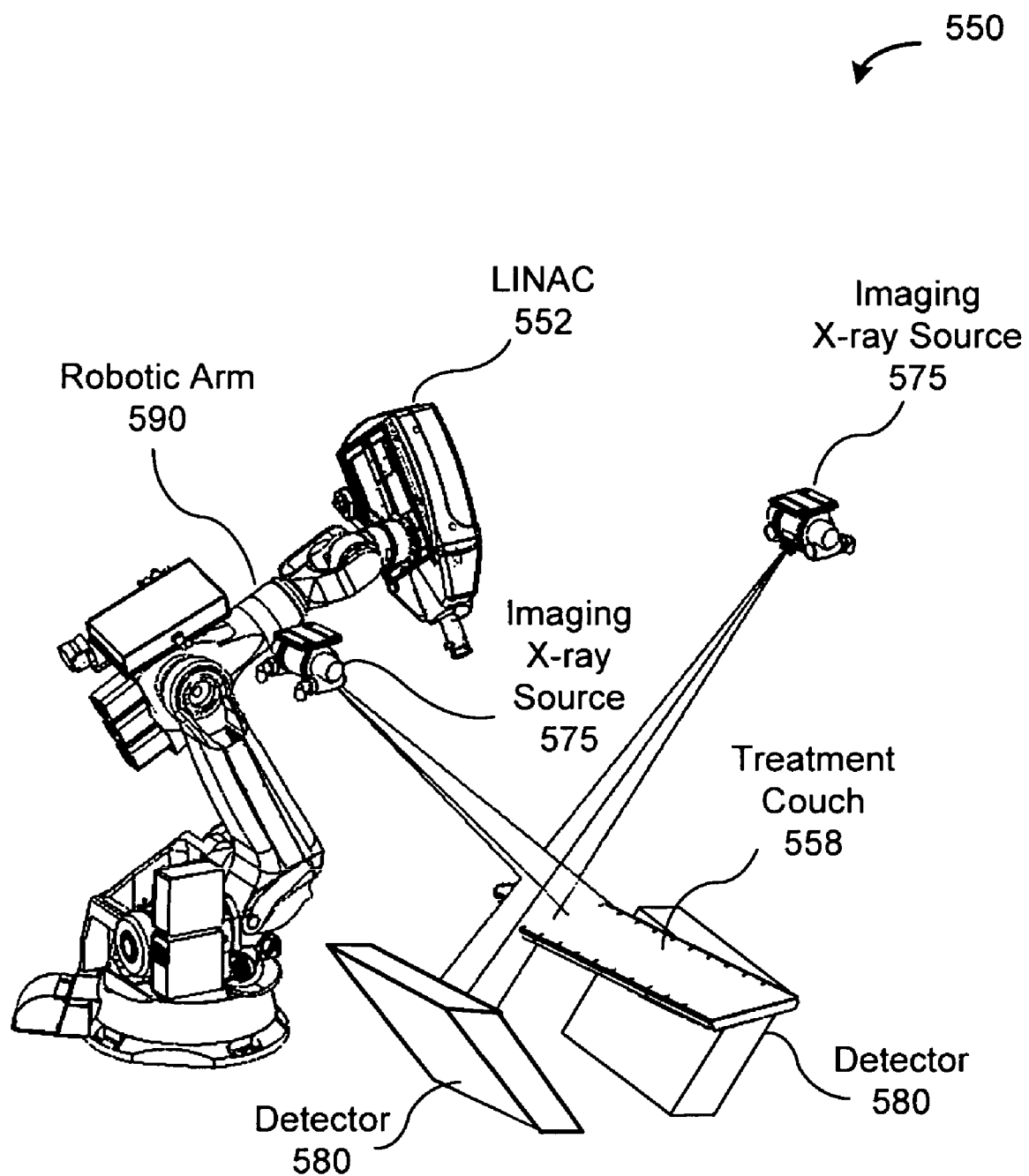
FIG. 11 is a schematic block diagram illustrating one embodiment of a treatment delivery system.

FIG. 11 is a schematic block diagram illustrating one embodiment of a treatment delivery system 550. The depicted treatment delivery system 550 includes a radiation source 552, in the form of a linear accelerator (LINAC), and a treatment couch 558, as described above. The treatment delivery system 550 also includes multiple imaging x-ray sources 575 and detectors 580. The two x-ray sources 575 may be nominally aligned to project imaging x-ray beams through a patient from at least two different angular positions (e.g., separated by 90 degrees, 45 degrees, etc.) and aimed through the patient on the treatment couch 558 toward the corresponding detectors 580. In another embodiment, a single large imager may be used to be illuminated by each x-ray imaging source 575. Alternatively, other quantities and configurations of imaging sources 575 and detectors 580 may be used. In one embodiment, the treatment delivery system 550 may be an image-guided, robotic-based radiation treatment system (e.g., for performing radiosurgery) such as the CyberKnife® system developed by Accuray Incorporated of California.

In the illustrated embodiment, the LINAC 552 is mounted on a robotic arm 590. The robotic arm 590 may have multiple (e.g., 5 or more) degrees of freedom in order to properly position the LINAC 552 to irradiate a target such as a pathological anatomy with a beam delivered from many angles in an operating volume around the patient. The treatment implemented with the treatment delivery system 550 may involve beam paths with a single isocenter (point of convergence), multiple isocenters, or without any specific isocenters (i.e., the beams need only intersect with the pathological target volume and do not necessarily converge on a single point, or isocenter, within the target). Furthermore, the treatment may be delivered in either a single session (mono-fraction) or in a small number of sessions (hypo-fractionation) as determined during treatment planning. In one embodiment, the treatment delivery system 550 delivers radiation beams according to the treatment plan without fixing the patient to a rigid, external frame to register the intra-operative position of the target volume with the position of the target volume during the pre-operative treatment planning phase.

As described above, the digital processing system 556 may implement algorithms to register images obtained from the imaging system 554 with pre-operative treatment planning images obtained from the diagnostic imaging system 510 in order to align the patient on the treatment couch 558 within the treatment delivery system 550. Additionally, these images may be used to precisely position the radiation source 552 with respect to the target volume or target.

In one embodiment, the treatment couch 558 may be coupled to second robotic arm (not shown) having multiple degrees of freedom. For example, the second arm may have five rotational degrees of freedom and one substantially vertical, linear degree of freedom. Alternatively, the second arm may have six rotational degrees of freedom and one substantially vertical, linear degree of freedom. In another embodiment, the second arm may nave at least four rotational degrees of freedom. Additionally, the second arm may be vertically mounted to a column or wall, or horizontally mounted to pedestal, floor, or ceiling. Alternatively, the treatment couch 558 may be a component of another mechanism, such as the AXUM® treatment couch developed by Accuray Incorporated of California. In another embodiment, the treatment couch 558 may be another type of treatment table, including a conventional treatment table.

Although one exemplary treatment delivery system 550 is described above, the treatment delivery system 550 may be another type of treatment delivery system. For example, the treatment delivery system 550 may be a gantry based (isocentric) intensity modulated radiotherapy (IMRT) system, in which a radiation source 552 (e.g., a LINAC) is mounted on the gantry in such a way that it rotates in a plane corresponding to an axial slice of the patient. Radiation may be delivered from several positions on the circular plane of rotation. In another embodiment, the treatment delivery system 550 may be a stereotactic frame system such as the GammaKnife®, available from Elekta of Sweden.

Figure 12:
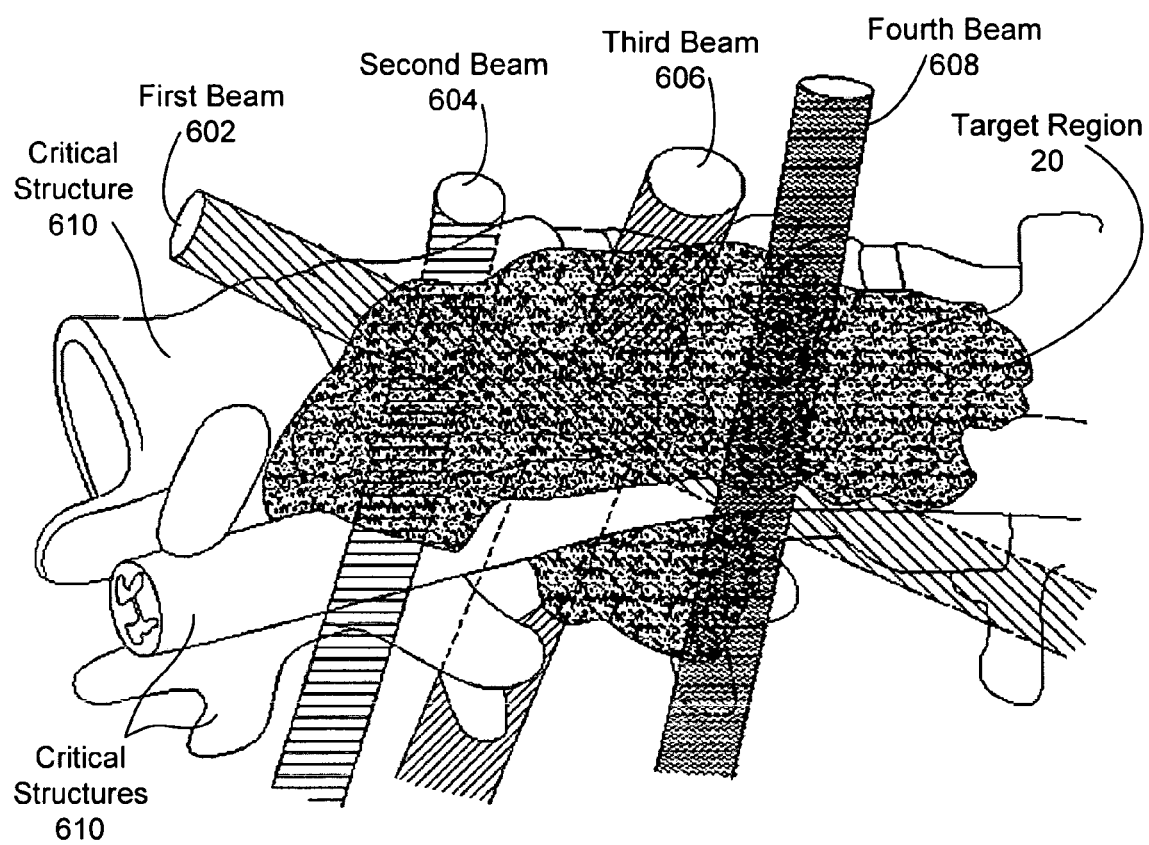
FIG. 12 illustrates a three-dimensional perspective view of a radiation treatment process.

FIG. 12 illustrates a three-dimensional perspective view of a radiation treatment process. In particular, FIG. 12 depicts several radiation beams directed at a target 20. In one embodiment, the target 20 may be representative of an internal organ, a region within a patient, a pathological anatomy such as a tumor or lesion, or another type of object or area of a patient. The target 20 also may be referred to herein as a target region, a target volume, and so forth, but each of these references is understood to refer generally to the target 20, unless indicated otherwise.

The illustrated radiation treatment process includes a first radiation beam 602, a second radiation beam 604, a third radiation beam 606, and a fourth radiation beam 608. Although four radiation beams are shown, other embodiments may include fewer or more radiation beams. For convenience, reference to one radiation beam is representative of all of the radiation beams, unless indicated otherwise. Additionally, the treatment sequence for application of the radiation beams may be independent of their respective ordinal designations.

In one embodiment, the four radiation beams are representative of beam delivery based on conformal planning, in which the radiation beams pass through or terminate at various points within target region 20. In conformal planning, some radiation beams may or may not intersect or converge at a common point in three-dimensional space. In other words, the radiation beams may be non-isocentric in that they do not necessarily converge on a single point, or isocenter. However, the radiation beams may wholly or partially intersect at the target 20 with one or more other radiation beams.

In another embodiment, the intensity of each radiation beam may be determined by a beam weight that may be set by an operator or by treatment planning software. The individual beam weights may depend, at least in part, on the total prescribed radiation dose to be delivered to target 20, as well as the cumulative radiation dose delivered by some or all of the radiation beams. For example, if a total prescribed dose of 3500 cGy is set for the target 20, the treatment planning software may automatically predetermine the beam weights for each radiation beam in order to balance conformality and homogeneity to achieve that prescribed dose.

In the depicted embodiment, the various radiation beams are directed at the target region 20 so that the radiation beams do not intersect with the critical structures 610. In another embodiment, the radiation beams may deliver radiation treatment to the target region 20 by sweeping across the target region 20, as described above. The beam sweeping radiation treatment may be effectuated or facilitated by the relative movement between the target region 20 and the beam paths of the individual radiation beams.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of a beam(s) and "target" may refer to a non-anatomical object or area.

Embodiments of the present invention include various operations, which are described herein. These operations may be performed by hardware components, software, firmware, or a combination thereof. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

The digital processing device(s) described herein may include one or more general-purpose processing devices such as a microprocessor or central processing unit, a controller, or the like. Alternatively, the digital processing device may include one or more special-purpose processing devices such as a digital signal processor (DSP), an application specific integrated circuit (ASIC), a field programmable gate array (FPGA), or the like. In an alternative embodiment, for example, the digital processing device may be a network processor having multiple processors including a core unit and multiple microengines. Additionally, the digital processing device may include any combination of general-purpose processing device(s) and special-purpose processing device(s).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   delivering, during a current treatment session, a portion of a radiation treatment to a target region of a patient based on a treatment plan, wherein the treatment plan comprises a plan dose;
   determining a delivery dose of the radiation treatment delivered to the target region based on tracking a movement of the target region relative to the position of a radiation beam used to deliver the dose; and
   modifying, before the current treatment session is completed, a subsequent portion of the radiation treatment based on a determination that the delivery dose is different from the plan dose, wherein modifying comprises recalculating the treatment plan using one or more modified inputs to the treatment plan.

2. The method of claim 1, further comprising comparing the delivery dose to the plan dose to identify the difference between the delivery dose and the plan dose.

3. The method of claim 1, wherein modifying the subsequent portion of the radiation treatment comprises modifying the current session of the radiation treatment.

4. The method of claim 3, wherein modifying the current session of the radiation treatment comprises terminating the treatment session.

5. The method of claim 1, wherein modifying the subsequent portion of the radiation treatment further comprises modifying a subsequent session of the radiation treatment.

6. The method of claim 1, further comprising providing real-time feedback to an operator, wherein the real-time feedback comprises the determined delivery dose or another dose value derived from the determined delivery dose.

7. The method of claim 1, wherein determining the delivery dose comprises ascertaining a dose delivery condition, wherein a treatment delivery system delivers the radiation therapy.

8. The method of claim 7, wherein the dose delivery condition comprises a delivery parameter known to the treatment delivery system.

9. The method of claim 8, wherein the delivery parameter comprises at least one of a patient position, a model correlation, a beam orientation, a beam activation, a beam intensity, or another beam characteristic.

10. The method of claim 1, further comprising suspending the radiation treatment in response to a determination that the radiation treatment exceeds a dose threshold.

11. A machine readable medium having instructions thereon, which instructions, when executed by a digital processing device, cause the digital processing device to perform the operations of claim 1.

12. The method of claim 1, wherein the one or more modified inputs comprises an off-axis correction ratio.

13. The method of claim 1, wherein the one or more modified inputs comprises a source-axis distance.

14. The method of claim 1, wherein the one or more modified inputs comprises a tissue maximum ratio.

15. The method of claim 1, wherein the one or more modified inputs comprises an output factor associated with a collimator.

16. The method of claim 1, wherein tracking the movement of the target region comprises fiducial tracking.

17. The method of claim 1, wherein tracking the movement of the target region comprises soft tissue tracking.

18. The method of claim 1, wherein tracking the movement of the target region comprises skeletal tracking.

19. A method, comprising:
    delivering a portion of a radiation treatment by a treatment delivery system to a target region of a patient based on a treatment plan, wherein the treatment plan comprises a plan dose condition;
    determining a delivery dose condition of the radiation treatment delivered to the target region based on tracking a movement of the target region relative to the position of a radiation beam, used to deliver the dose; and
    modifying a subsequent portion of the radiation treatment based on a determination that the delivery dose condition is different from the plan dose condition, wherein modifying comprises recalculating the treatment plan using one or more modified inputs to the treatment plan, wherein the dose delivery condition comprises an external factor measurable by the treatment delivery system.

20. The method of claim 19, wherein the external factor comprises a humidity measurement, an air pressure measurement, or a temperature measurement.

21. A method, comprising:
    delivering a portion of a radiation treatment to a target region of a patient based on a treatment plan, wherein the treatment plan comprises a plan dose;
    determining a delivery dose of the radiation treatment delivered to the target region, using a four-dimensional tissue deformation model, based on tracking a movement of the target region relative to the position of a radiation beam, used to deliver the dose; and
    modifying a subsequent portion of the radiation treatment based on a determination that the delivery dose is different from the plan dose, wherein modifying comprises recalculating the treatment plan using one or more modified inputs to the treatment plan.

22. A method, comprising:
    delivering, during a current treatment session, a portion of a radiation treatment to a target region based on a treatment plan, wherein the treatment plan comprises a plan condition;
    measuring an actual delivery condition corresponding to the plan condition, wherein measuring the actual delivery condition comprises tracking the target region during the treatment delivery; and
    implementing, during the current treatment session, a treatment delivery modification during the treatment delivery based on a difference between the actual delivery condition and the plan condition.

23. The method of claim 22, further comprising:
    measuring the actual delivery condition over the delivered portion of the radiation treatment; and
    wherein implementing further comprises implementing the treatment delivery modification during a subsequent portion of the radiation treatment.

24. The method of claim 22, further comprising comparing the actual delivery condition to the plan condition to identify the difference between the actual delivery condition and the plan condition.

25. The method of claim 22, wherein implementing the treatment delivery modification comprises changing one or more treatment plan parameters.

26. The method of claim 22, wherein implementing the treatment delivery modification comprises terminating the treatment delivery.

27. The method of claim 22, further comprising generating the treatment delivery modification by calculating a position parameter or a dose parameter based on the actual delivery condition.

28. The method of claim 22, wherein the plan condition comprises a planned target region position and measuring the actual delivery condition comprises determining an actual target region position.

29. The method of claim 22, wherein the plan condition comprises a planned radiation source position and measuring the actual delivery condition comprises determining an actual radiation source position.

30. The method of claim 22, wherein the plan condition comprises a planned radiation source orientation and measuring the actual delivery condition comprises determining an actual radiation source orientation.

31. The method of claim 22, wherein the plan condition comprises a planned humidity and measuring the actual delivery condition comprises measuring an actual humidity.

32. The method of claim 22, wherein the plan condition comprises a planned temperature and measuring the actual delivery condition comprises measuring an actual temperature.

33. The method of claim 22, wherein the plan condition comprises a planned air pressure and measuring the actual delivery condition comprises measuring an actual air pressure.

34. The method of claim 22, wherein the plan condition comprises a planned calibration and measuring the actual delivery condition comprises determining an actual calibration.

35. The method of claim 22, wherein measuring the actual delivery condition comprises calculating an actual delivered dose.

36. An apparatus, comprising:
a radiation source to deliver a radiation beam to a target region of a patient based on a treatment plan, wherein the treatment plan comprises a plan dose; and
a digital processing device coupled to the radiation source, the digital processing device to determine a delivery dose of the radiation beam delivered to the target region based on tracking a movement of the target region relative to the position of a radiation beam, used to deliver the dose, during a current treatment session, and to modify, before the current treatment session is completed, a subsequent radiation beam based on a determination that the delivery dose is different from the plan dose by recalculating the treatment plan using one or more modified inputs to the treatment plan.

37. The apparatus of claim 36, wherein the digital processing device is further configured to compare the delivery dose to the plan dose to identify the difference between the delivery dose and the plan dose.

38. The apparatus of claim 36, wherein the radiation treatment modification comprises a modification to a current session of the radiation treatment.

39. The apparatus of claim 36, wherein the radiation treatment modification comprises a modification to a subsequent session of the radiation treatment.

40. The apparatus of claim 36, further comprising a user interface coupled to the digital processing device, the user interface to provide real-time feedback to an operator, wherein the real-time feedback comprises the determined delivery dose or another dose value derived from the determined delivery dose.

41. The apparatus of claim 36, further comprising a memory device coupled to the digital processing device, the memory device to store a dose delivery condition.

42. The apparatus of claim 41, wherein the memory device is further configured to store a dose threshold, wherein the digital processing device is further configured to suspend the radiation treatment in response to a determination that a cumulative delivery dose exceeds the dose threshold.

43. The apparatus of claim 41, wherein the dose delivery condition is a delivery parameter, the delivery parameter comprising a patient position parameter, a model correlation parameter, a beam orientation parameter, a beam activation parameter, a beam intensity parameter, or another beam characteristic.

44. The apparatus of claim 36, further comprising a multi-leaf collimator coupled to the radiation source to modify a field geometry of the radiation beam.

45. The apparatus of claim 44, wherein the multi-leaf collimator comprises an attenuation leaf to attenuate an intensity of at least a portion of the radiation beam.

46. A system comprising the apparatus of claim 36, the system further comprising a treatment planning system coupled to the digital processing device, the treatment planning system to generate the treatment plan.

47. The system of claim 46, further comprising a diagnostic imaging system coupled to the treatment planning system, the diagnostic imaging system to generate an image of the target region and communicate a representation of the image to the treatment planning system.

48. The system of claim 47, further comprising:
an imaging system coupled to the digital processing device, the imaging system to determine a real-time position of the target region relative to the radiation source;
a user interface coupled to the digital processing device;
a memory device coupled to the digital processing device; and
a measurement device coupled to the digital processing device.

49. An apparatus, comprising:
a radiation source to deliver a radiation beam to a target region of a patient based on a treatment plan, wherein the treatment plan comprises a plan dose;
a digital processing device coupled to the radiation source, the digital processing device to determine a delivery dose of the radiation beam delivered to the target region based on tracking a movement of the target region relative to the position of a radiation beam, used to deliver the dose, and to modify a subsequent radiation beam based on a determination that the delivery dose is different from the plan dose by recalculating the treatment plan using one or more modified inputs to the treatment plan;
a memory device coupled to the digital processing device, the memory device to store a dose delivery condition; and
a measurement device coupled to the digital processing device, the measurement device comprising a hygrometer to measure humidity, a barometer to measure air pressure, or a thermometer to measure temperature, wherein the dose delivery condition is an external factor, the external factor comprising a humidity measurement, an air pressure measurement, or a temperature measurement.

* * * * *